US012643076B2

(12) United States Patent (10) Patent No.: US 12,643,076 B2
Linic et al. (45) Date of Patent: Jun. 2, 2026

(54) CATALYST SYSTEM FOR DEHYDROGENATION

(71) Applicant: REGENTS OF THE UNIVERSITY OF MICHIGAN, Ann Arbor, MI (US)

(72) Inventors: Suljo Linic, Ann Arbor, MI (US); James Wortman, Ann Arbor, MI (US); Rawan Almallahi, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 318 days.

(21) Appl. No.: 18/376,332

(22) Filed: Oct. 3, 2023

(65) Prior Publication Data

US 2024/0116006 A1 Apr. 11, 2024

Related U.S. Application Data

(60) Provisional application No. 63/378,234, filed on Oct. 3, 2022.

(51) Int. Cl.
| | |
|---|---|
| *B01D 69/14* | (2006.01) |
| *B01D 53/22* | (2006.01) |
| *B01D 69/08* | (2006.01) |
| *B01D 71/02* | (2006.01) |
| *B01J 21/08* | (2006.01) |
| *B01J 23/62* | (2006.01) |
| (Continued) | |

(52) U.S. Cl.
CPC ........... *B01D 69/145* (2013.01); *B01D 53/22* (2013.01); *B01D 69/08* (2013.01); *B01D 71/025* (2013.01); *B01J 21/08* (2013.01); *B01J 23/626* (2013.01); *B01J 35/45* (2024.01); *B01J 35/59* (2024.01); *B01J*

*35/647* (2024.01); *B01J 37/0201* (2013.01); *C07C 5/48* (2013.01); *B01D 2257/108* (2013.01); *C07C 2523/62* (2013.01)

(58) Field of Classification Search
CPC ...... B01D 69/145; B01D 53/22; B01D 69/08; B01D 71/025; B01D 2257/108; B01D 69/02; B01D 2325/04; B01D 69/10; B01D 69/148; B01D 71/022; B01D 71/027; B01D 53/228; B01J 21/08; B01J 23/626; B01J 35/45; B01J 35/59; B01J 35/647; B01J 37/0201; C07C 5/48; C07C 2523/62; C07C 2523/14; C07C 2523/42; C07C 5/3337
USPC .......................................................... 585/658
See application file for complete search history.

(56) References Cited

U.S. PATENT DOCUMENTS 5,214,227 A     5/1993   Zhou et al.
2020/0269208 A1*  8/2020   Way ...................... B01D 69/02

OTHER PUBLICATIONS

"Nanoporous Zeolite—A sheltered PD0Hoolow Fiber catalystic membrane reactor for propane Dehydrogenation" ACS appl. Nano matter 2020, 3, 6675-6683 (Year: 2020).*

(Continued)

*Primary Examiner* — Prem C Singh
*Assistant Examiner* — Francis C Campanell
(74) *Attorney, Agent, or Firm* — MARSHALL, GERSTEIN & BORUN LLP

(57) ABSTRACT

A catalyst system for propane dehydrogenation includes a hollow fiber members packed with a $Pt_1Sn_1/SiO_2$ catalyst. The hollow fiber membrane includes a separation layer coated on an interior surface of a support tube. The separation layer selectively removes $H_2$ generated during the propane dehydrogenation reaction.

20 Claims, 29 Drawing Sheets

(51) Int. Cl.

| | |
|---|---|
| *B01J 35/45* | (2024.01) |
| *B01J 35/59* | (2024.01) |
| *B01J 35/64* | (2024.01) |
| *B01J 37/02* | (2006.01) |
| *C07C 5/48* | (2006.01) |

(56) References Cited

OTHER PUBLICATIONS

"H2 reduction behaviors and catalytic performance of bimetallic tin-modified platinum catalysts for propane dehydrogenation" J. of Molecular catalysts A Chemical 184 (2002) 203-213 (Year: 2002).*
A. Bariås et al., Propane Dehydrogenation over Supported Pt and Pt—Sn Catalysts: Catalyst Preparation, Characterization, and Activity Measurements, Journal of Catalysis, 158(1): 1-12(1996).
Agarwal et al., Sustainable Process Design Approach for On-Purpose Propylene Production and Intensification, ACS Sustainable Chem. Eng, 6(2): 2407-2421(2018).
Armor, Applications of catalytic inorganic membrane reactors to refinery products, Journal of Membrane Science, 147(2): 217-233(1998).
Battersby et al., An analysis of the Peclet and Damkohler numbers for dehydrogenation reactions using molecular sieve silica (MSS) membrane reactors, Catalysis Today, 116(1): 12-17(2006).
Bhasin et al., Dehydrogenation and oxydehydrogenation of paraffins to olefins, Applied Catalysis A: General, 221(1-2): 397-419(2001).
Carrero et al., Critical Literature Review of the Kinetics for the Oxidative Dehydrogenation of Propane over Well-Defined Supported Vanadium Oxide Catalysts, ACS Catal, 4(10): 3357-3380(2014).
Chen et al., Propane dehydrogenation: catalyst development, new chemistry, and emerging technologies, Chem. Soc. Rev, 50(5): 3315-3354(2021).
Choi et al., Material properties and operating configurations of membrane reactors for propane dehydrogenation, Alche Journal, 61(3): 922-935(2015).
Choi et al., Modeling and process simulation of hollow fiber membrane reactor systems for propane dehydrogenation, Alche Journal, 63(10): 4519-4531(2017).
Cola et al., Non-oxidative propane dehydrogenation over Pt—Zn-containing zeolites, Applied Catalysis A: General, 306(1): 85-97(2006).
Collins et al., Catalytic Dehydrogenation of Propane in Hydrogen Permselective Membrane Reactors, Ind. Eng. Chem. Res, 35(12): 4398-4405(1996).
De Vos et al., High-Selectivity, High-Flux Silica Membranes for Gas Separation, Science, 279(5357): 1710-1711(1998).
Deng et al., Behavior of active species on Pt—Sn/SiO2 catalyst during the dehydrogenation of propane and regeneration, Applied Catalysis A: General, 606(1): (2020).
Feng et al., Carbon deposition during propane dehydrogenation in a fuel cell, Journal of Power Sources, 167(2): 486-490(2007).
Gbenedio et al., A multifunctional Pd/alumina hollow fibre membrane reactor for propane dehydrogenation, Catalysis Today, 156(3-4): 93-99(2010).
Gokhale et al., Effects of reactant loss and membrane selectivity on a dehydrogenation reaction in a membrane-enclosed catalytic reactor, Journal of Membrane Science, 103(3): 235-242(1995).
Grant et al., Selective oxidative dehydrogenation of propane to propene using boron nitride catalysts, Science, 354(6319): 1570-1573(2016).
Gu et al., Hydrothermally stable silica-alumina composite membranes for hydrogen separation, Journal of Membrane Science, 310(1-2): 28-37(2008).
Gu et al., Permeation properties and hydrothermal stability of silica-titania membranes supported on porous alumina substrates, Journal of Membrane Science, 345(1-2): 267-275(2009).
Hannagan et al., First-principles design of a single-atom-alloy propane dehydrogenation catalyst, 372(6549): 1444-1447(2021).
Iglesias-Juez et al., A combined in situ time-resolved UV-Vis, Raman and high-energy resolution X-ray absorption spectroscopy study on the deactivation behavior of Pt and Ptsingle bondSn propane dehydrogenation catalysts under industrial reaction conditions, Journal of Catalysis, 276(2): 268-279(2010).
Jiang et al., Propane Dehydrogenation over Pt/TiO2—Al2O3 Catalysts, ACS Catal, 5(1): 438-447(2015).
Kärger et al., Diffusion in Nanoporous Materials, Wiley, 1(1): 85-110 (2012).
Kaylor et al., Propane dehydrogenation over supported Pt—Sn nanoparticles, Journal of Catalysis, 367(1): 181-193(2018).
Kim et al., Thin Hydrogen-Selective SAPO-34 Zeolite Membranes for Enhanced Conversion and Selectivity in Propane Dehydrogenation Membrane Reactors, Chem. Mater, 28(12): 4397-4402(2016).
Larsson et al., The Effect of Reaction Conditions and Time on Stream on the Coke Formed during Propane Dehydrogenation, Journal of Catalysis, 164(1): 44-53(1996).
Li et al., Coke Formation on Pt—Sn/Al2O3 Catalyst in Propane Dehydrogenation: Coke Characterization and Kinetic Study, Topics in Catalysis, 54(888): 888-896(2011).
Li et al., Dehydrogenation of light alkanes to mono-olefins, Chem. Soc. Rev, 50(7): 4359-4381(2021).
Liu et al., Structural modulation and direct measurement of subnanometric bimetallic PtSn clusters confined in zeolites, Nature Catalysis, 3(1): 628-638(2020).
Lobera et al., Transient kinetic modelling of propane dehydrogenation over a Pt—Sn—K/Al2O3 catalyst, Applied Catalysis A: General, 349(1-2): 156-164(2008).
Mansoor et al., Recent Developments in Natural Gas Flaring Reduction and Reformation to Energy-Efficient Fuels: A Review, Energy Fuels, 35(5): 3675-3714(2021).
Moon et al., Design guide of a membrane for a membrane reactor in terms of permeability and selectivity, Journal of Membrane Science, 170(1): 43-51(2000).
Morejudo et al., Direct conversion of methane to aromatics in a catalytic co-ionic membrane reactor, Science, 353(6299): 563-566(2016).
Motagamwala et al., Stable and selective catalysts for propane dehydrogenation operating at thermodynamic limit, Science, 372(6551): 217-222(2021).
National Academies of Sciences et al., The Changing Landscape of Hydrocarbon Feedstocks for Chemical Production, Implications for Catalysis: Proceedings of a Workshop, (2016).
Otroshchenko et al., Current status and perspectives in oxidative, non-oxidative and CO2-mediated dehydrogenation of propane and isobutane over metal oxide catalysts, Chem. Soc. Rev, 50(1): 473-527(2021).
Pati et al., Nanoporous Zeolite-A Sheltered Pd-Hollow Fiber Catalytic Membrane Reactor for Propane Dehydrogenation, ACS Appl. Nano Mater, 3(7): 6675-6683(2020).
Pham et al., Role of Sn in the Regeneration of Pt/?—Al2O3 Light Alkane Dehydrogenation Catalysts, ACS Catal, 6(4): 2257-2264(2016).
Qu et al., Low-Temperature Direct Dehydrogenation of Propane over Binary Oxide Catalysts: Insights into Geometric Effects and Active Sites, ACS Sustainable Chem. Eng, 9(38): 12755-12765(2021).
Rebo et al., Deactivation of Pt—Sn catalyst in propane dehydrogenation, Studies in Surface Science and Catalysis, 126(1): 333-340(1999).
Saerens et al., The Positive Role of Hydrogen on the Dehydrogenation of Propane on Pt(111), ACS Catal, 7(11): 7495-7508(2017).
Saito et al., Effect of physically adsorbed water molecules on the H2-selective performance of a silica membrane prepared with dimethoxydiphenylsilane and its regeneration, Journal of Membrane Science, 392-393(1): 95-100(2012).
Sakbodin et al., Direct Nonoxidative Methane Conversion in an Autothermal Hydrogen-Permeable Membrane Reactor, Advanced Energy Materials, 11(46): (2021).

(56)          References Cited

OTHER PUBLICATIONS

Salmones et al., H2 reduction behaviors and catalytic performance of bimetallic tin-modified platinum catalysts for propane dehydrogenation, Journal of Molecular Catalysis A: Chemical, 184(1-2): 203-213(2002).

Sattler et al., Catalytic Dehydrogenation of Light Alkanes on Metals and Metal Oxides, Chem. Rev, 114(20): 10613-10653(2014).

Sattler et al., Catalytic limitations on alkane dehydrogenation under H2 deficient conditions relevant to membrane reactors, Energy Environ. Sci, 15(5): 2120-2129(2022).

Schafer et al., Comparison of different catalysts in the membrane-supported dehydrogenation of propane, 82(1-4): 15-23(2003).

Sint Annaland et al., A kinetic rate expression for the time-dependent coke formation rate during propane dehydrogenation over a platinum alumina monolithic catalyst, Catalysis Today, 66(2-4): 427-436(2001).

Song et al., Improved Effect of Fe on the Stable NiFe/Al2O3 Catalyst in Low-Temperature Dry Reforming of Methane, Ind. Eng. Chem. Res, 59(39): 17250-17258(2020).

Sun et al., A comparative study on different regeneration processes of Pt—Sn/?—Al2O3 catalysts for propane dehydrogenation, Journal of Energy Chemistry, 27(1): 311-318(2018).

Sun et al., Subnanometer Bimetallic Platinum-Zinc Clusters in Zeolites for Propane Dehydrogenation, Angewandte Chemie, 132(44): 19618-19627(2020).

Wang et al., High H2 permeable SAPO-34 hollow fiber membrane for high temperature propane dehydrogenation application, Alche Journal, 66(9): e16278 (2020).

Wang et al., On the Role of Sn Segregation of Pt—Sn Catalysts for Propane Dehydrogenation, ACS Catal, 11(8): 4401-4410(2021).

Wang et al., Stabilizing the isolated Pt sites on PtGa/Al2O3 catalyst via silica coating layers for propane dehydrogenation at low temperature, Applied Catalysis B: Environmental, 300(1): 120731 (2022).

Weyten et al., Dehydrogenation of propane using a packed-bed catalytic membrane reactor, Alche Journal, 43(7): 1819-1827(1997).

Weyten et al., Membrane performance: the key issues for dehydrogenation reactions in a catalytic membrane reactor, Catalysis Today, 56(1-3): 3-11(2000).

Wu et al., A novel inorganic hollow fiber membrane reactor for catalytic dehydrogenation of propane, Alche Journal, 55(9): 2389-2398(2009).

Zhang et al., Sn-Modified ZSM-5 as Support for Platinum Catalyst in Propane Dehydrogenation, Ind. Eng. Chem. Res, 50(13): 7896-7902(2011).

Zhao et al., Molecular understandings on the activation of light hydrocarbons over heterogeneous catalysts, Chem. Sci, 6(8): 4403-4425(2015).

Ziaka et al., A high temperature catalytic membrane reactor for propane dehydrogenation, Journal of Membrane Science, 77(2-3): 221-232(1993).

* cited by examiner

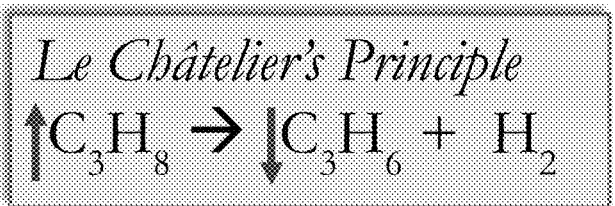
A
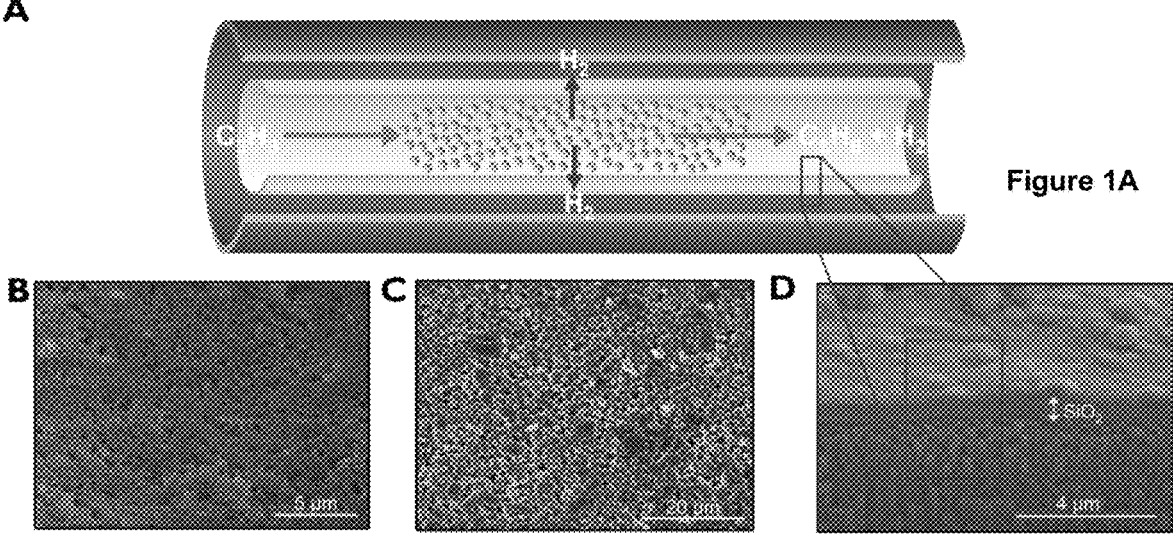
Figure 1A
B        C        D
Figure 1B        Figure 1C        Figure 1D
E
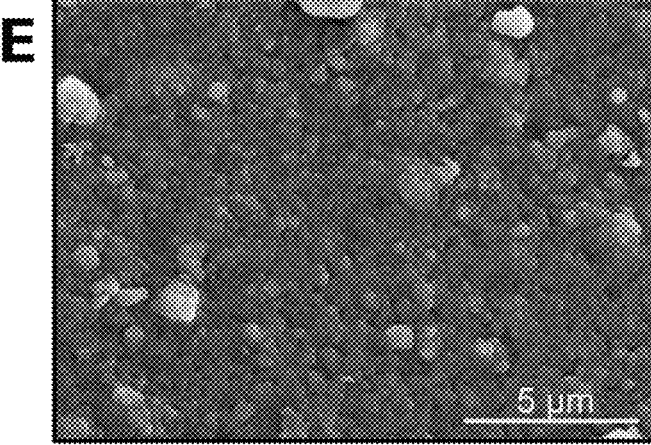
Figure 1E

A

B

A

B

A

B

A

B

Cross-section $$Da = \frac{reaction\ rate}{convective\ mass\ transport\ rate}$$

$$Pe = \frac{convective\ mass\ transport\ rate}{H_2\ membrane\ transport\ rate}$$

Temperature – 580 °C,
Pressure – 1 atm

A

B

Shell side

Tube side

A

B

C

A

B

CATALYST SYSTEM FOR DEHYDROGENATION

CROSS-REFERENCE TO RELATED APPLICATION

The benefit of priority to U.S. Provisional Application No. 63/378,234 filed Oct. 3, 2022, is hereby claimed and the disclosure is incorporated herein by reference in its entirety.

STATEMENT OF GOVERNMENT SUPPORT

This invention was made government support under grant nos. DE EE0007888 and DGE 1256260 awarded by the National Science Foundation. The government has certain rights in the invention.

FIELD

The disclosure relates to a catalyst system for a dehydrogenation reaction, which includes a hollow fiber packed with a dehydrogenation catalyst.

BACKGROUND

Propylene is one of the most diverse building blocks in the petrochemical industry. It is used in the production of a range of chemicals such as polypropylene, propylene oxide, and acrylonitrile. Conventional methods for propylene production include large scale, centralized naphtha steam and fluid catalytic cracking. These processes; however, suffer from low selectivity to propylene and high energy requirements. Additionally, recent surge in relatively abundant shale gas has caused a shift in feedstock from oil-based naphtha to shale-based ethane. Steam cracking of ethane results in little to no propylene production, leading to the so-called propylene supply gap where the demand for propylene is projected to be higher than the supply.

One way to alleviate this problem is to develop technologies that can convert propane, another shale gas component that is currently flared, directly into propylene in a distributed fashion that is commensurate with the shale gas supply chain. Propane dehydrogenation (PDH) is an emerging technology for direct production of propylene and hydrogen ($H_2$). PDH is an endothermic reaction requiring elevated reaction temperatures to achieve considerable propane conversions and propylene yields (FIG. 8). Under these high temperature conditions, the rates of undesired side reactions such as propane cracking and the formation of solid carbon on the catalysts surface are more thermodynamically favored (FIG. 9), leading to low selectivity and rapid catalyst deactivation, requiring frequent and costly catalyst regeneration. For example, the commercial Catofin, chromium-based, catalyst alternates between dehydrogenation, regeneration, and purge steps within 15-30 minutes cycles.

A strategy that has been proposed to address the problem of low equilibrium conversion is to couple a PDH catalyst to a $H_2$-permeable membrane to form a catalyst/membrane chemical conversion system. In this design, $H_2$ molecules, formed during PDH, are removed from the reaction zone using a separation membrane. This $H_2$ removal shifts the reaction equilibrium toward the product side according to Le Châtelier's principle, and hence propane conversion is enhanced. Although a membrane design adds to fabrication costs, the increased product yields can reduce downstream separation requirements (separating propane and propylene is challenging) and limit operational costs. An additional potential advantage of the membrane/catalysts system is that it could allow for system operation at lower temperatures, therefore, limiting undesired cracking and catalyst poisoning side reactions.

This catalyst/membrane strategy has been challenged by numerous obstacles that have prevented not only its practical applications but also its rigorous testing. One obstacle is the limited availability of selective $H_2$ transporting membranes that can operate under these conditions. Previous studies have attempted to employ metal-based (palladium), zeolite, and oxide-based membranes. Most of these membranes suffer from low $H_2$ permeability, high cost, susceptibility to sintering, embrittlement, and deactivation by carbon deposition (coking) under the PDH conditions. Another very significant obstacle to the development of catalyst/membrane systems is that the commercial PDH catalysts are not viable for these systems since they are designed to operate at $H_2$ partial pressures that are higher than the equilibrium pressure. For example, commercial platinum (Pt)-based PDH catalysts (used in the Oleflex process) require additional $H_2$ to be added to the reactive feed to alleviate some of the problems with catalyst stability discussed above. This addition of $H_2$ is highly undesirable in the catalyst/membrane systems as it lowers the equilibrium PDH conversion. In fact, effective catalyst/membrane systems require a catalyst that can operate in a $H_2$ depleted regime, where $H_2$ is removed from the product mixture. Due to these catalyst stability issues, most previous studies of catalyst/membrane systems have utilized catalyst materials that suffer from severe deactivation, relying on collecting reaction data only at initial points (i.e., at time=zero) or operating in extremely diluted propane mixtures, which are practically not viable. Some of these studies even had to resort to co-feeding $H_2$ with propane, which while having a positive effect on catalyst stability, lowers the thermodynamic conversion limits and defeats the purpose of the catalyst/membrane integration.

SUMMARY

A catalyst system for a dehydrogenation reaction in accordance with the disclosure can include a hollow fiber membrane comprising an outer support tube formed of a porous support material and a separation layer formed on an inner surface of the support tube such that the separation layer substantially covers the inner surface of the support tube, the separation layer comprising $SiO_2$, and a dehydrogenation catalyst packed inside the hollow fiber membrane, the dehydrogenation catalyst comprising $Pt_1Sn_1$ arranged on a $SiO_2$ support, wherein a ratio of a surface area to the volume of the catalyst system is about 500 $m^2/m^3$ to about 3000 $m^2/m^3$ and an amount of catalysts exposed on the membrane surface of about 300 $g/m^2$ to about 1500 $g/m^2$.

A dehydrogenation process catalyzed by the catalyst system in accordance with the disclosure can include flowing a reactant source through the catalyst system such that the propane source flows in contact with the catalyst packed within the hollow fiber and upon contact with the catalyst is selectively dehydrogenated, and $H_2$ generated during the selective dehydrogenation is selectively removed through the separation layer, wherein the process has a selectivity of at least 90%.

A dehydrogenation process catalyzed by the catalyst system in accordance with the disclosure can include flowing a reactant source through the catalyst system such that the propane source flows in contact with the catalyst packed within the hollow fiber and upon contact with the catalyst is selectively dehydrogenated, and $H_2$ generated during the selective dehydrogenation is selectively removed through the separation layer, and flowing a sweeping gas comprising $O_2$ over an outer surface of the tube to oxidize $H_2$ separated from the dehydrogenation reaction thereby forming water and heat. The process can have a selectivity of at least 90%.

BRIEF DESCRIPTION OF THE DRAWINGS

FIG. 1A is a schematic illustration of a catalyst system in accordance with the disclosure;

FIG. 1B is an SEM image of the inner surface of an uncoated $Al_2O_3$ hollow fiber membrane (before $SiO_2$ deposition);

FIG. 1C is an SEM image of an outer surface of an $SiO_2/Al_2O_3$ hollow fiber membrane in accordance with the disclosure showing the porous alumina substrate;

FIG. 1D is an SEM image of a cross section of an $SiO_2/Al_2O_3$ hollow fiber membrane in accordance with the disclosure, showing the layered $SiO_2/Al_2O_3$ structure;

FIG. 1E is an SEM image of an inner surface an $SiO_2/Al_2O_3$ hollow fiber membrane in accordance with the disclosure, showing the topmost smooth $SiO_2$ layer;

DETAILED DESCRIPTION

Catalyst systems in accordance with the disclosure include a hollow fiber membrane packed with a dehydrogenation catalyst. The dehydrogenation catalyst includes a dehydrogenation catalytic material disposed on support. The support included in dehydrogenation catalyst and the hollow fiber membrane material can both include silica. The hollow fiber membrane advantageously is $H_2$ permeable and removes $H_2$ generated during the dehydrogenation reaction. This multicomponent catalyst system has been observed to operate at conversions that exceeded the thermodynamic limits of the dehydrogenation reaction. The catalyst systems of the disclosure can achieve enhanced propane conversion above the equilibrium limit with complete selectivity and excellent stability. The catalysts of the disclosure can allow for expansion of the operational dehydrogenation temperature range to lower temperatures, while retaining high conversion and reaction rates. This can significantly improve overall stability of the materials under the harsh, reducing reaction conditions of the dehydrogenation reaction.

FIG. 1A is a schematic illustration of a catalyst system in accordance with the disclosure. The catalyst system has an asymmetric and porous tubular hollow fiber with a thin $SiO_2$ separation layer on the inner side of a supporting tube. The tube can be formed by a porous $Al_2O_3$ layer or multi-layer structure. The dehydrogenation catalyst is packed inside of the fiber membrane (referenced herein as the tube side), in contact with the separation layer. An inert gas can be flowed on the other, outer side of the fiber membrane (referenced herein as the shell side).

Figure 24:
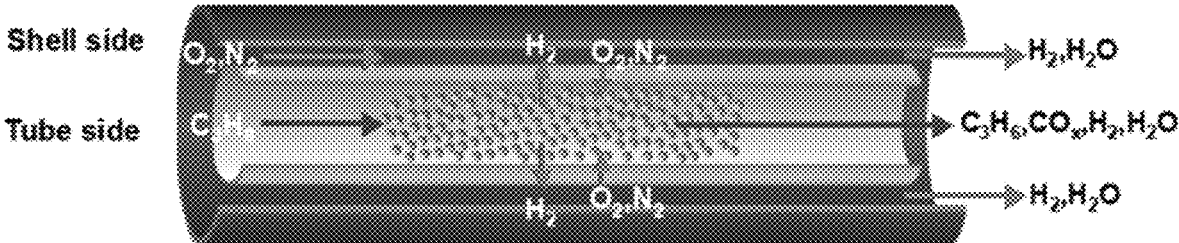
FIG. 24 is a schematic illustration of a catalyst system in accordance with the disclosure and use of the catalyst system with an $O_2$ content in the sweeping gas flow.

FIG. 24 is a schematic illustration of a catalyst system in accordance with the disclosure providing for PDH and $H_2$ oxidation. The catalyst system is similar to that of FIG. 1A, but the system is operated with an additional introduction of $O_2$ on the shell side of the catalyst system. The $O_2$ flow interacts with the $H_2$ transported from the tube side where the PDH occurs in an exothermic process to produce water and release heat. As $H_2$ is removed by the membrane and oxidized on the shell side, water is formed. It was observed that water formation rates increased as $O_2$ levels were increased.

The catalyst can be a $Pt_1Sn_1$ dehydrogenation catalyst material disposed on a support. The support can be, for example, $SiO_2$. This catalyst alone was observed to be a selective propane dehydrogenation catalyst that operates at the thermodynamic conversion limit with a propylene selectivity of >99% without any addition of $H_2$. The catalyst is also suitable for ethane dehydrogenation. The catalyst includes $Pt_1Sn_1$, nanoparticles supported on silica ($SiO_2$). The nanoparticles can be about 2 nm in diameter.

The hollow fiber membrane is an $H_2$ permeable membrane. The membrane can include a separation layer that selectively separates $H_2$ from during the dehydrogenation reaction. The separation layer can be, for example, $SiO_2$. The hollow fiber membrane includes a support tube upon which the separation layer is supported. The support tube can be, for example, an alumina tube. The $SiO_2$ separation layer can be coated on the inside of the tube. The separation layer can entirely or substantially entirely cover the inner surface of the tube.

Figure 10:
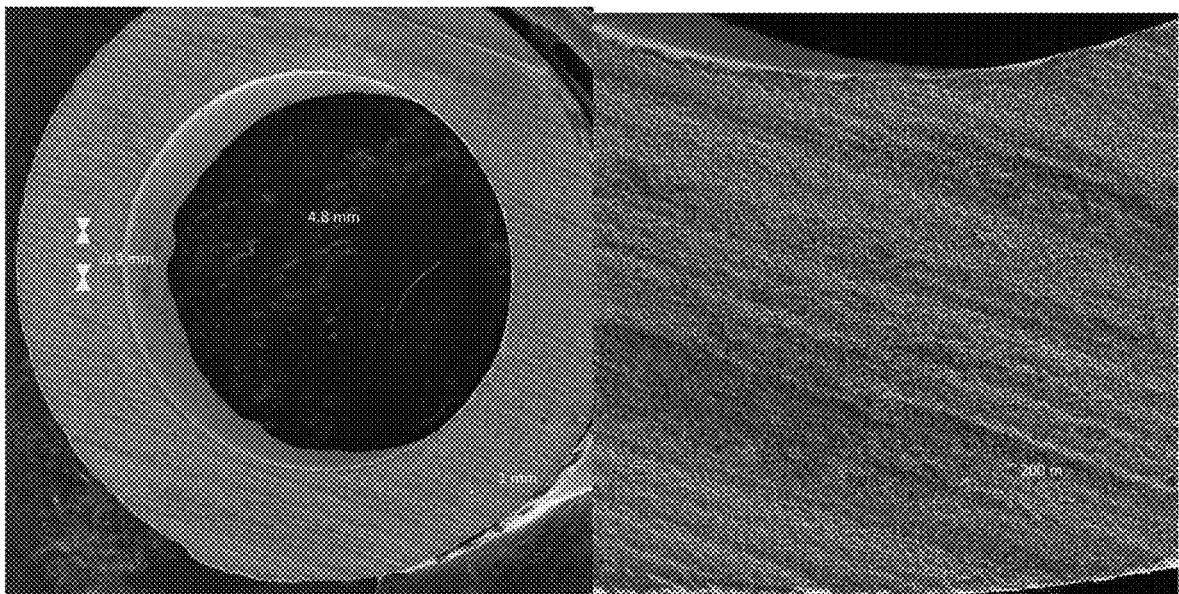
FIG. 10 includes top-down SEM characterization images of the $Al_2O_3$ membrane confirming fiber diameter and wall thickness dimensions.

The hollow fiber membrane can have an outer diameter of about 1.5 mm to about 6 mm, about 3 mm to about 6 mm, about 2 mm to about 4 mm, or about 1 mmm to about 5 mm. Other suitable diameters include about 1.5, 2, 2.5, 3, 3.5, 4, 4.5, 5, 5.5, or 6 mm and any ranges defined by such values and any values there between. The support tube wall can have a thickness of about 0.5 mm to about 1.5 mm, about 1 mm to 1.5 mm, or about 0.7 mm to about 0.9 mm. Other suitable thicknesses include about 0.5, 0.6, 0.7, 0.8, 0.9, 1, 1.1, 1.2, 1.3, 1.4, 1.5 and any ranges defined by such values and any values there between. For example, FIG. 10 shows a porous $Al_2O_3$ tube having an outer diameter of about 4.8 mm and a wall thickness of 0.9 mm.

The tube can be formed of one or more layers. For example, an $Al_2O_3$ tube can be formed two $Al_2O_3$ layers. The outer layer can have a thickness of about 250 micrometers to about 750 micrometers, about 300 micrometers to about 500 micrometers, or about 400 micrometers to about 650 micrometers. Other suitable thicknesses include about 250, 300, 350, 400, 450, 500, 550, 600, 650, 700, 750, and any ranges defined by such values and any values there between.

The outer layer can have an average pore size of about 100 nm to about 500 nm, about 250 nm to about 400 nm, about 200 nm to about 350 nm, or about 150 nm to about 500 nm. Other suitable average pore sizes include about 100, 150, 200, 250, 300, 350, 400, 450, 500 and any ranges defined by such values and any values there between.

The inner layer can have a thickness of about 0.5 micrometers to about 20 micrometers, about 0.5 micrometers to about 5 micrometers, about 10 micrometers to about 20 micrometers, about 7 micrometers to about 15 micrometers or about 1 micrometer to about 10 micrometers. Other suitable thicknesses include about 0.5, 1, 1.5, 2, 2.5, 3, 3.5, 4, 4.5, 5, 5.5, 6, 6.5, 7, 7.5, 8, 8.5, 9, 9.5, 10, 12, 14, 16, 18, 20, and any ranges defined by such values and any values there between.

The inner layer can have an average pore size of about 5 nm to about 50 nm, about 10 nm to about 50 nm, about 20 nm to about 40 nm, or about 15 nm to about 35 nm. Other suitable average pore sizes include about 5, 6, 7, 8, 9, 10, 12, 14, 16, 18, 20, 22, 24, 26, 28, 30, 32, 34, 36, 38, 40, 42, 44, 46, 48, 50 and any ranges defined by such values and any values there between. For example, an $Al_2O_3$ tube of the hollow fiber membrane can include an outer layer having a thickness of about 860 micrometers and an average pore size of about 200 nm, and an inner layer having a thickness of about 10 micrometers and a 20 nm average pore size.

Referring to FIGS. 1B and 1C, and SEM image of the inner surface of an $Al_2O_3$ tube formed of two layers is shown. FIG. 1B is an SEM image of the inner surface of the tube, showing a clear porous surface. FIG. 1C is an SEM of the outer surface of the tube, showing large particles of a large pore size distribution.

The separation layer can be deposited on the inner surface of the supporting tube using any known methods such as CVD. For example, a $SiO_2$ separation layer can be deposited on an $Al_2O_3$ tube through chemical vapor deposition of tetraethyl orthosilicate (TEOS) at 600° C. The separation layer can be $SiO_2$ or a $SiO_2$ composite. Composite silica membranes can be formed of silica and one or more of alumina, titania, zirconia, and zeolite materials. The composite structure can be useful for stabilize the silica membranes, such as for use in humid conditions. For example, composite silica membranes can be useful when catalysis occurs with hydrothermal conditions.

The separation layer can have a thickness of about 20 nm to about 500 nm, about 50 nm to about 300 nm, about 100 nm to about 450 nm, or about 20 nm to about 75 nm. Other suitable thicknesses include about 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 nm and any ranges defined by such values and any values there between. The separation layer can have a porosity of about 2 nm to about 20 nm, about 10 nm to about 15 nm, about 2 nm to about 12 nm, or about 5 nm to about 18 nm. Other suitable values include about 2, 3, 4, 5, 6, 7, 8, 9, 10, 11, 12, 13, 14, 15, 16, 17, 18, 19, 20 nm and any ranges defined by such values and any values there between.

The catalyst system of the disclosure can have a ratio of the surface area to the volume of the system of about 500 m2/m 3 to about 3000 $m^2/m^3$, about 1000 $m^2/m^3$ to about 2500 $m^2/m^3$, or about 800 $m^2/m^3$ to about 1500 $m^2/m^3$. Other suitable ratios include about 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000 $m^2/m^3$, and any ranges defined by such values and any values there between.

The catalyst system of the disclosure advantageously has a high surface area of catalyst exposed within the membrane for interaction with the reactants to be catalyzed. For example, the amount of catalyst exposed on the surface area of the membrane can be about 300 g/m$^2$ to about 1500 g/m$^2$, about 500 g/m$^2$ to about 1000 g/m$^2$ or about 700 g/m$^2$ to about 1500 g/m$^2$. Other suitable amounts of catalyst exposed per membrane surface area include about 300, 350, 400, 450, 500, 550, 600, 650, 700, 750, 800, 850, 900, 950, 1000, 1050, 1100, 1150, 1200, 1250, 1300, 1350, 1400, 1450, 1500 g/m$^2$, and any ranges defined by such values and any values there between.

The catalyst system of the disclosure allows for high surface area of the $H_2$ transporting medium without compromising the PDH catalyst surface area. Hollow fibers membranes of the disclosure can provide the needed high surface area of the transport medium with small diameters. Hollow fiber geometries in accordance with the disclosure can allow for high membrane surface areas per volume of reactor, such as up to 1000 $m^2/m^3$. This can lead to significant lowering of the overall reactor volumes for achieving desired conversion. The membrane has been observed to selectively remove $H_2$ produced during the dehydrogenation reaction at a removal rate that effectively shifts the dehydrogenation equilibrium towards a higher conversion and yields. Catalyst systems of the disclosure have been observed to have enhancements of up to 10% in propane conversion above the equilibrium limit with improved selectivity and excellent stability.

Catalyst systems of the disclosure can be useful for dehydrogenation reactions such as, but not limited to, propane dehydrogenation and ethane dehydrogenation.

Catalyst systems of the disclosure can catalyze a reaction by flowing the reactant source (e.g., a propane or ethane source) through the catalyst system in contact with the catalyst packed within the hollow fiber membrane. Upon contact with the catalysts, the reactant within the reactant source is selectively dehydrogenated. For example, in a propane dehydrogenation reaction, the catalyst when in contact with propane from the propane source selectively dehydrogenates the propane to propylene. $H_2$ generated during the selective dehydrogenation is selectively removed through the separation layer. The catalyst system has a selectivity of at least 90%.

The catalyst system can operate at temperatures lower than conventional systems, for example, a temperature range of about 400° C. to about 600° C.

Dehydrogenation reactions using the catalyst system of the disclosure can advantageously be performed without the need for added $H_2$.

An inert sweeping gas can be flowed over the outer surface of the catalyst system, that is the outer side of the tube) to carry away $H_2$ separated during the dehydrogenation reaction. Any inert gas can be used, including, one or more of Ar, He, Ne, Kr, Xe, and Rn. Additionally, the sweeping gas can include $O_2$ to provide for oxidation of $H_2$ on the shell side. The $O_2$ can be present in the sweeping gas in an amount of 6% to 15% by volume based on the total volume of the sweeping gas. The sweeping gas can include an inert gas and $O_2$.

The sweeping gas containing $O_2$ can be flowed on the shell side during the process to oxidize the $H_2$ released during the processes and thereby form water. The oxidation is an exothermic reaction producing heat. Heat exchange can be provided such that the heat generated by the exothermic reaction can be used in the process to heat the catalyst system to the temperature needed for the dehydrogenation reaction. The process can be performed with or without applied heat from an external source. For example, the heat generated by the exothermic oxidation of $H_2$ can provide sufficient heat for the dehydrogenation process, such that applied heat from an external source is not needed or can be discontinued after initiation of the reaction. For example, the process can include a flowing a sweeping gas having about 10% by volume to about 15% by volume $O_2$ and the process can be performed without applied heat.

The Damkohler (Da) and Peclet (Pe) numbers were two dimensionless numbers considered in the design of the catalyst systems of the disclosure. The Da number is described by the ratio of the reaction rate and the convective transport rate of the reactant through the reactor. It is closely related to the conversion that can be achieved in a system, with a larger Da number leading to larger conversion. The Pe number is the ratio of convective transport rate to the membrane permeation rate. A combination of high Da and low Pe numbers are desired for optimized performance, marked by a high reaction rate and a high $H_2$ permeation rate. Tuning of the geometries of the catalysts systems of the disclosure with consideration of Da and Pe numbers can lead to further enhancements in performance.

A performance metric that is often used to quantify the performance of a catalyst is the rate of conversion per gram of the catalyst. The inherent kinetic PDH reaction rates were analyzed using an integral reactor analysis for many catalysts reported in literature and compared it to the rates measured on the $Pt_1Sn_1/SiO_2$ catalyst used in the membrane system herein. The data in FIG. 3D and Table 2 show that the PDH rates on the $Pt_1Sn_1/SiO_2$ catalyst are in general comparable to the best performing Pt-based PDH catalysts, and significantly higher than the rates on non-Pt based materials.

Another performance metric in PDH is the selectivity to propylene as a function of propane conversion. In general, due to downstream separation process costs, it is highly desirable that the system can achieve close to 100% selectivity at high conversions. Data in FIG. 3E and Table 1 show the initial (fresh material) selectivity/conversion performance results for different PDH systems reported in literature. The comparative literature systems for most of these catalysts were operated in packed bed reactors (PBR) (data represented with triangles in the figure), with a limited number of studies employing catalyst/membrane systems (circles in the figure).

tivity at 500° C. As shown in FIG. 3E, the catalyst system of the disclosure had selectivity/conversion performance that was well above most other PBR catalysts and catalyst systems previously tested for propane dehydrogenation. Conventional catalysts generally suffer from poor selectivity or conversion.

Figure 4A:
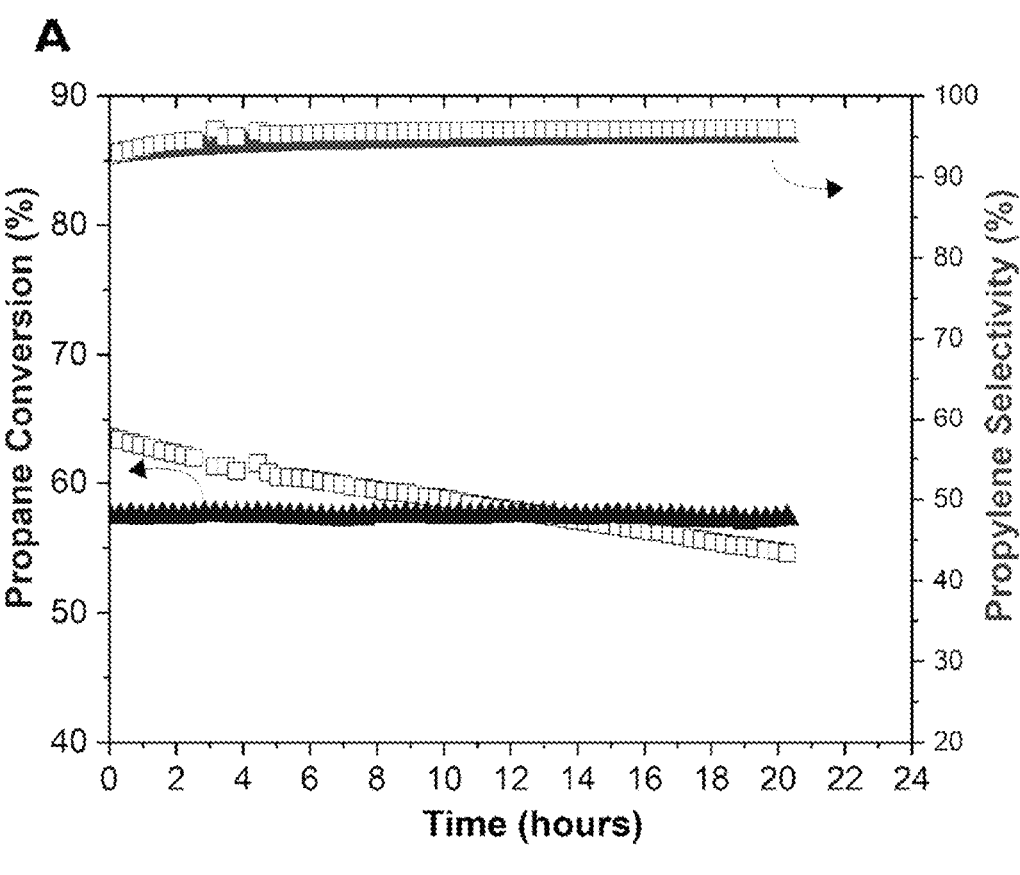
FIG. 4A is a graph showing propane conversion and propylene selectivity as a function of time for the catalyst system of the disclosure (square) compared to conventional PBR (triangle)

The catalyst system of the disclosure also demonstrated improved stability as compared to conventional PDH catalyst. Conventional catalysts have limited stability under PDH reaction conditions. Poor stability in these conventional systems is not surprising since they operate under carbon-rich, reducing conditions which are fertile for the formation of solid carbon deposits. These harsh conditions are further exacerbated by the removal of $H_2$. To overcome these difficulties, a large majority of previous studies of catalyst/membrane systems resorted to significant propane feed dilution and co-feeding $H_2$, which defeats the purpose of using the catalyst/membrane systems to shift reaction equilibrium conversion. Contrary to conventional systems and the expectation in the art, the catalyst systems of the disclosure have significantly improved stability as compared to conventional catalysts, even systems that resorted to feed dilution and co-feeding $H_2$. FIG. 4 shows propane conversion and propylene selectivity as a function of time obtained on the $Pt_1Sn_1/SiO_2$ catalyst/membrane system described in the examples at 580° C., in a pure propane stream, a WHSV of 1.3 h$^{-1}$ and a sweep:feed ratio of 10. The catalyst system of the disclosure deactivated slowly over time. The rate of

TABLE 1

| Catalyst, Membrane | Temp (° C.) | Feed Composition (vol %) [a] | Equilibrium conversion (%) | Conversion (%) [b] | Conversion/ equilibrium conversion | Selectivity (%) [b] | Ref. |
|---|---|---|---|---|---|---|---|
| 7.5 wt % Cr/Al$_2$O$_3$, SiO$_2$/Al$_2$O$_3$ | 500 | 100% C$_3$H$_8$ | 18 | 23.8 | 132.2 | 89 | (2) |
| PtSn/SiO$_2$, SiO$_2$/Al$_2$O$_3$ | 500 | 100% C$_3$H$_8$ | 24.7 | 33.7 | 136.4 | 99 | Catalyst system of the disclosure |
| PtSn/SiO$_2$, SiO$_2$/Al$_2$O$_3$ | 580 | 100% C$_3$H$_8$ | 52 | 64 | 123.1 | 95 | Catalysts of the disclosure |
| 1% Na$_2$O-doped 20% Cr$_2$O$_3$ 80% Al$_2$O$_3$, SAPO-34 | 600 | 100% C$_3$H$_8$ | 48 | 75 | 156.3 | 80 | (3) |
| 7.5 wt % Cr/Al$_2$O$_3$, Pd/Al$_2$O$_3$ | 600 | 30% C$_3$H$_8$ | 64.2 | 48 | 74.8 | 89 | (4) |

[a] Remainder is inert gas (either Helium or Nitrogen)
[b] Data presented here is the best conversion and selectivity reported in each article.
(2) - H. Weyten, K. Keizer, A. Kinoo, J. Luyten, R. Leysen, Dehydrogenation of propane using a packed-bed catalytic membrane reactor. AIChE Journal. 43, 1819-1827 (1997).
(3) - S.- J. Kim, Y. Liu, J. S. Moore, R. S. Dixit, J. G. Pendergast, D. Sholl, C. W. Jones, S. Nair, Thin Hydrogen-Selective SAPO-34 Zeolite Membranes for Enhanced Conversion and Selectivity in Propane Dehydrogenation Membrane Reactors. Chemistry of Materials. 28, 4397-4402 (2016).
(4) - S. Pati, N. Dewangan, Z. Wang, A. Jangam, S. Kawi, Nanoporous Zeolite-A Sheltered Pd-Hollow Fiber Catalytic Membrane Reactor for Propane Dehydrogenation. ACS Appl Nano Mater. 3, 6675-6683 (2020).

The catalyst system of the disclosure outperformed other systems with respect to selectivity/conversion performance metrics. For example, at 580° C., these catalyst systems reach ~123% propane conversion (relative to equilibrium conversion) with over 95% propylene selectivity. The performance can be even further improved relative to the thermodynamic equilibrium limit to over 140% conversion (relative to the eq. conversion) with 100% propylene selecdeactivation of the catalyst system of the disclosure was compared to the measured rates of deactivation of conventional systems in Table 1. To compute the rates of deactivation, the propane conversion data, reported as a function of time for different catalysts, were analyzed assuming first-order deactivation kinetics to calculate the catalyst deactivation coefficient, $k_d$, as is usually done for catalytic reactions on supported metal nanoparticles.

TABLE 2

| # | Catalyst, Membrane | Temperature (° C.) | Inverse deactivation coefficient, $1/k_d$ (h) | Initial forward rate (mol/g/s) | Conversion/ equilibrium conversion | Ref. |
|---|---|---|---|---|---|---|
| 1 | 7.5 wt % Cr/Al$_2$O$_3$, SiO$_2$/Al$_2$O$_3$ | 500 | 112 | 8.73E-7 | 132 | (2) |
| 2 | 1% Na$_2$O-doped 20% Cr$_2$O$_3$ 80% Al$_2$O$_3$, SAPO-34 | 600 | — | 8.31E-07 | 156.3 | (3) |
| 3 | 7.5 wt % Cr/Al$_2$O$_3$, Pd/Al$_2$O$_3$ | 600 | 9 | — | 75 | (4) |
| 4 | Pt-based/alumino silicate, SiO$_2$/Al$_2$O$_3$ | 550 | 23.813 | — | — | (5) |
| 5 | Pt/SBA-15, Pd/Al$_2$O$_3$ | 500 | 0.9323 | — | — | (6) |
| 6 | Pt/Al$_2$O$_3$, Pd/Ag/Al$_2$O$_3$ | 450 | 0.0869 | — | — | (7) |
| 7 | PtSn/SiO$_2$ | 580 | 262.7 | $4.28 \times 10^{-05}$ | 98.0 | (1) |
| 8 | PtSn/SiO$_2$ (diluted) | 580 | 100.9 | $8.52 \times 10^{-05}$ | 99.5 | (1) |
| 9 | Pt/Al$_2$O$_3$ | 580 | 5.32 | $5.02 \times 10^{-06}$ | 24.8 | (1) |
| 10 | PtSn/Al$_2$O$_3$ | 580 | 7.61 | $7.39 \times 10^{-06}$ | 34.6 | (1) |
| 11 | PtSn/Al$_2$O$_3$ | 580 | 31.7 | $1.74 \times 10^{-05}$ | 93.2 | (1) |
| 12 | Pt—Sn/Al$_2$O$_3$ | 519 | 8.53 | $4.10 \times 10^{-05}$ | 92.3 | (8) |
| 13 | Pt—Sn/MgAl$_2$O$_4$ | 550 | 30.5 | $2.34 \times 10^{-06}$ | 52.2 | (9) |
| 14 | Pt—Ga/ MgAl$_2$O$_4$ | 605 | 42.3 | $1.21 \times 10^{-05}$ | 73.6 | (10) |
| 15 | Pt—Sn/SiO$_2$ | 555 | 24.4 | $1.90 \times 10^{-05}$ | — | (11) |
| 16 | Pt—Na/Sn-ZSM-5 | 590 | 83.3 | $1.43 \times 10^{-05}$ | 88.2 | (12) |
| 17 | Pt—Zn/Na—Y | 555 | 21 | $6.76 \times 10^{-06}$ | 79 | (13) |
| 18 | Pt—Sn—Na/ Al-SBA-15 | 590 | 41.3 | $5.61 \times 10^{-06}$ | 58.1 | (14) |
| 19 | Pt/Mg(Ga)(Al) O | 600 | 5.1 | $6.16 \times 10^{-05}$ | 28.6 | (15) |
| 20 | Pt/Mg(In)(Al)O | 600 | 7.28 | $8.30 \times 10^{-05}$ | 36.4 | (16) |
| 21 | Meso. CrO$_x$/Al$_2$O$_3$ | 580 | 1.9 | $1.86 \times 10^{-06}$ | 19 | (17) |
| 22 | Cr$_2$O$_3$-pillared on ZrP | 550 | 4.2 | $2.28 \times 10^{-06}$ | 26.5 | (18) |
| 23 | Ga—Cr mixed oxide on ZrP | 550 | 2.4 | $3.76 \times 10^{-06}$ | 40.5 | (19) |
| 24 | CrO$_x$/ZrO$_2$ | 550 | 3.8 | $1.76 \times 10^{-06}$ | 73.6 | (20) |
| 25 | Cr—Si—Zr on Xerogel | 450 | 8.3 | $1.08 \times 10^{-06}$ | 83.4 | (21) |
| 26 | Cr—Na/Al$_2$O$_3$ | 550 | 14.5 | $5.25 \times 10^{-07}$ | 75.3 | (22) |
| 27 | Ga$_2$O$_3$/SiO$_2$ | 550 | 2.8 | $4.03 \times 10^{-07}$ | 36.9 | (23) |
| 28 | B—Ga$_2$O$_3$ | 500 | 4.8 | $3.60 \times 10^{-07}$ | 51.3 | (24) |
| 29 | Ga$_2$O$_3$ | 600 | 1.5 | $2.72 \times 10^{-07}$ | 42.7 | (25) |
| 30 | Ga$_2$O$_3$/ZrO$_2$ | 600 | 1.3 | $8.51 \times 10^{-07}$ | 42.0 | (26) |
| 31 | Ga$_5$Al$_5$O$_{15}$ | 500 | 5.9 | $7.65 \times 10^{-07}$ | 80.4 | (27) |
| 32 | Ga$_5$Al$_2$O$_{15}$ | 500 | 11.2 | $7.02 \times 10^{-07}$ | 77.3 | (27) |
| 33 | 0.35 wt % PtSn/Al$_2$O$_3$-nanosheet | 590 | 146 | $2.27 \times 10^{-03}$ | 97.4 | (28) |
| 34 | 0.5% Pt-0.9% Sn/Al$_2$O$_3$ | 590 | 82.6 | $6.81 \times 10^{-04}$ | 97 | (29) |
| 35 | PtSn/CeO$_2$ | 680 | 26.6 | $3.90 \times 10^{-05}$ | 49.5 | (30) |
| 36 | K-PtSn@MFI-22 h | 600 | 76.7 | $7.70 \times 10^{-03}$ | 55.3 | (31) |
| 37 | Pt-Sn/SiO$_2$ | 500 | — | $2.38 \times 10^{-03}$ | | (32) |
| 38 | Pt-Sn/SiO$_2$ | 500 | 28.8 | $3.02 \times 10^{-03}$ | 84.1 | (33) |
| 39 | K-PtSn@MFI | 600 | 83.8 | $4.72 \times 10^{-03}$ | 100 | (34) |
| 40 | PtSn/SiO$_2$, SiO$_2$/Al$_2$O$_3$ | 580 | 57.2 | 2.18E-5 | 123 | This work |
| 41 | PtSn/SiO$_2$, SiO$_2$/Al$_2$O$_3$ | 500 | 3015 | 5.72E-6 | 136 | This work |

Figure 4B:
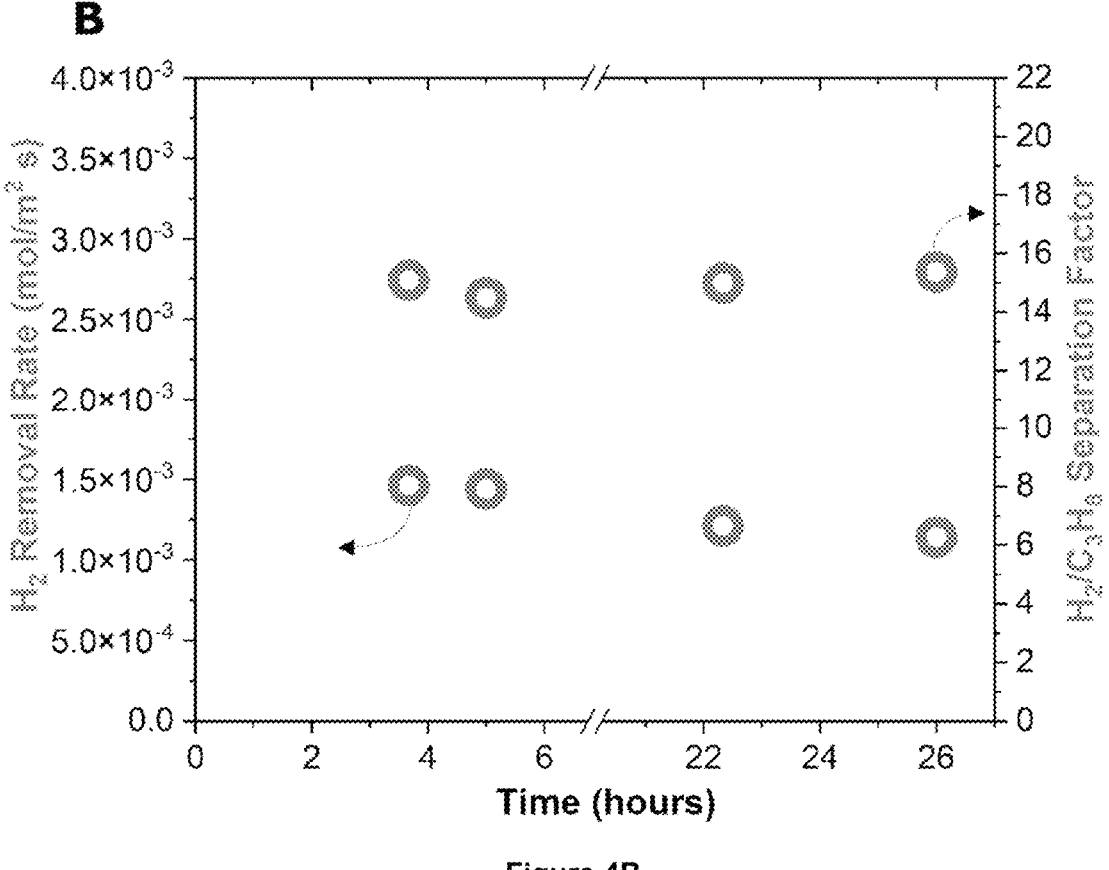
FIG. 4B is a graph showing $H_2$ removal rate and the $H_2/C_3H_8$ separation factor as a function of time for a catalyst system in accordance with the disclosure. Reaction temperature was 580° C., $P_{c3H8}$=1, WHSV=1.3 hours$^{-1}$ and sweep: feed=b 10.

Without intending to be bound by theory, it is believed that the decline in the performance of the catalyst system of the disclosure is related to a gradual deactivation of the $P_1Sn_1$ catalyst due to the formation of solid carbon on catalyst surface, which is a general feature of propene dehydrogenation processes. FIG. 4B show that the performance of the membrane was stable over time under the reaction conditions. FIG. 4B shows the measured $H_2$ removal rate and the $H_2/C_3H_8$ separation factor as a function of time for the stability experiments shown in FIG. 4A. Although the $H_2$ removal rate slightly decreases over time (due to the decreasing propane conversion, i.e., lower $H_2$ produced), the results show that membrane can perform selective separation ($H_2/C_3H_8$ separation factor=15) for a long period of time despite the high-reducing, coke-forming environment.

Figure 15:
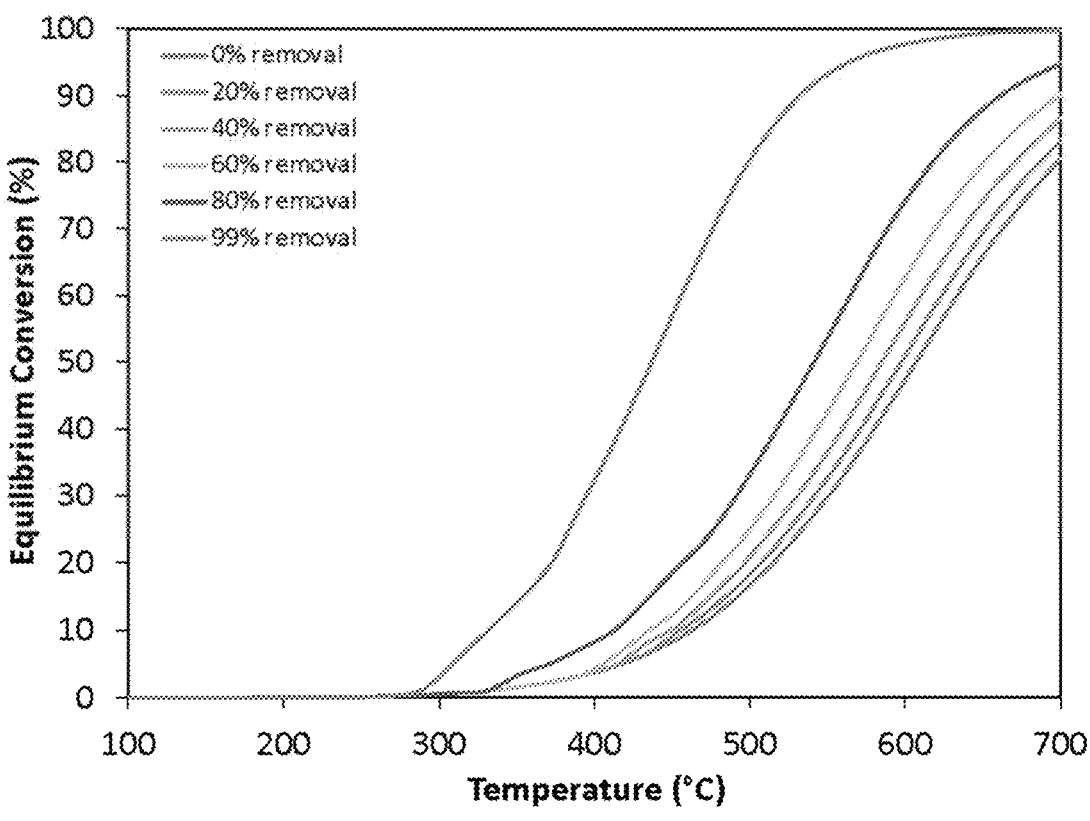
FIG. 15 is a graph showing equilibrium conversion for propane dehydrogenation as a function of temperature for different levels of $H_2$ removal.
Figure 16:
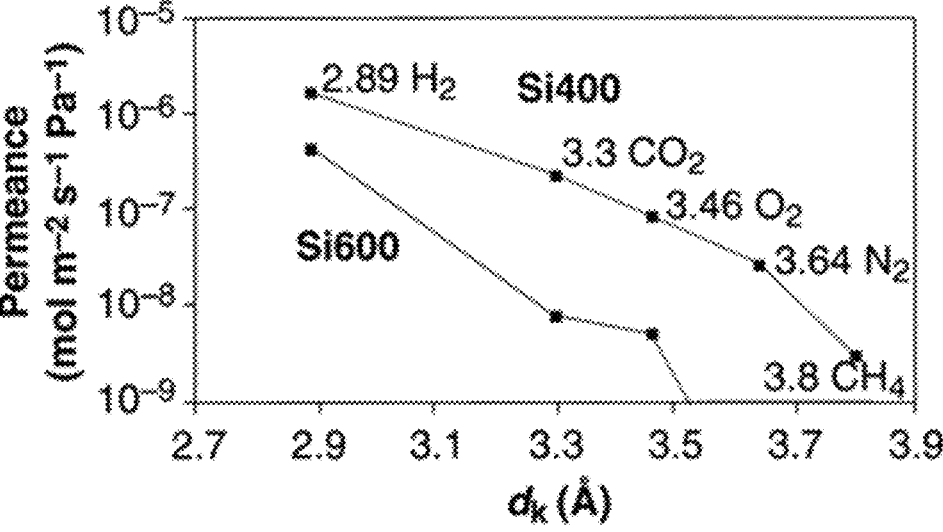
FIG. 16 is a graph showing permeance of a catalyst system in accordance with the disclosure.
Figure 17:
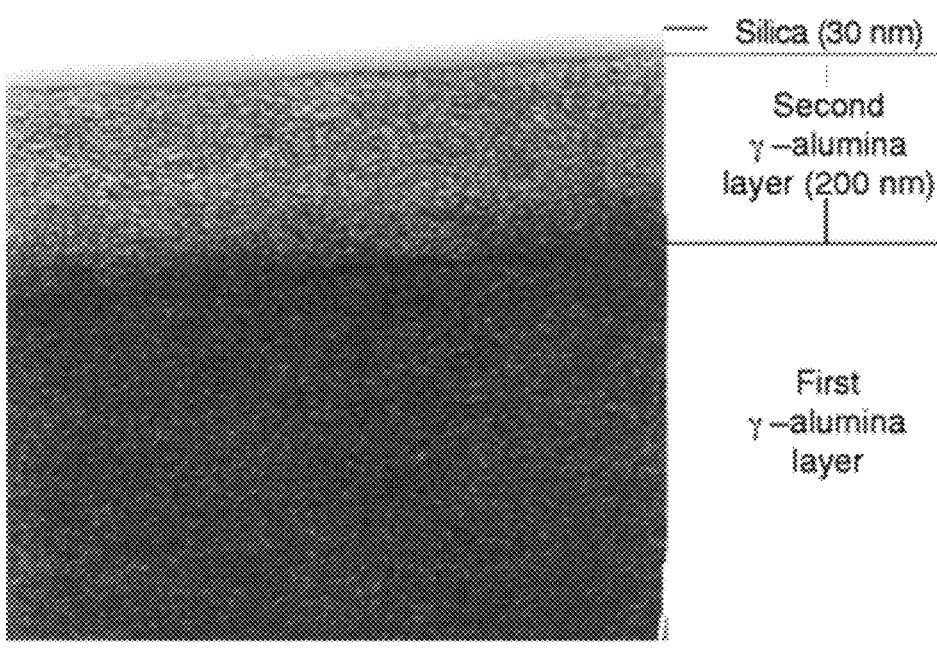
FIG. 17 is an SEM image of a cross-section of a membrane in accordance with the disclosure.
Figure 18:
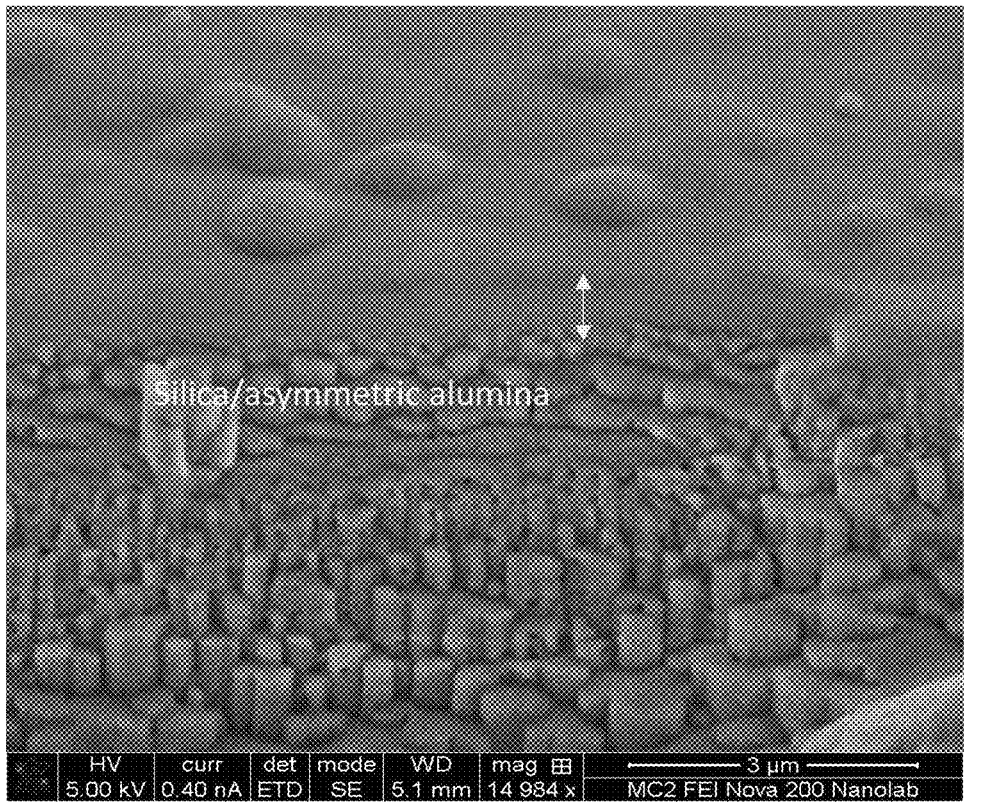
FIG. 18 is an SEM image of a cross-section showing an about 360 nm silica layer on an asymmetric alumina support.
Figure 19:
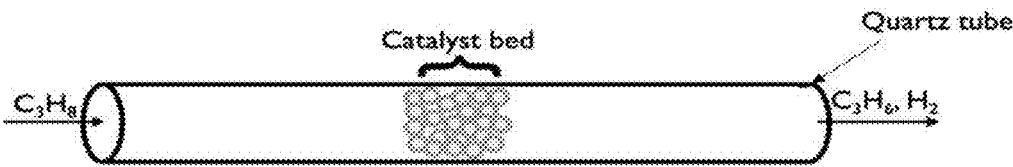
FIG. 19 is a schematic illustration for calculations used in assessing the catalyst system in accordance with the disclosure, where Da is a measure of whether the residence time is sufficient to reach equilibrium and Pe evaluates the effectiveness of the membrane in removing a desired product from the reaction zone.
Figure 19:
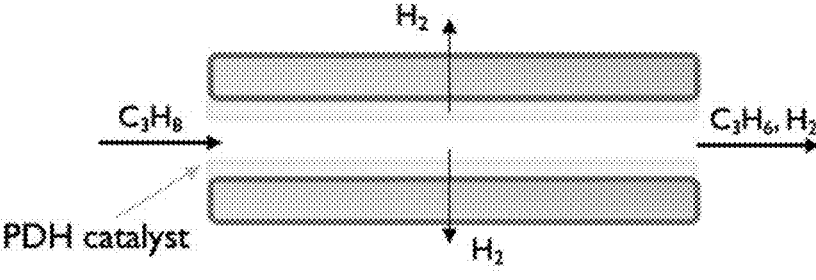
Figure 20A:
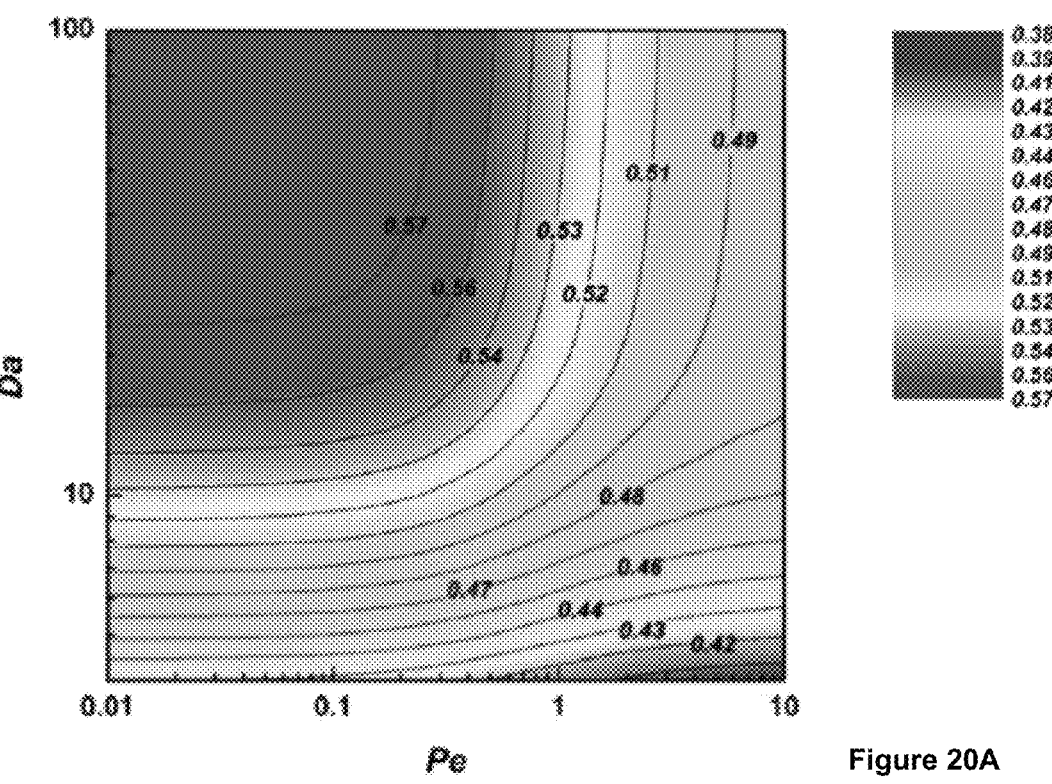
FIG. 20A is a graph showing Da as a function of Pe for a catalyst system in accordance with the disclosure.
Figure 20B:
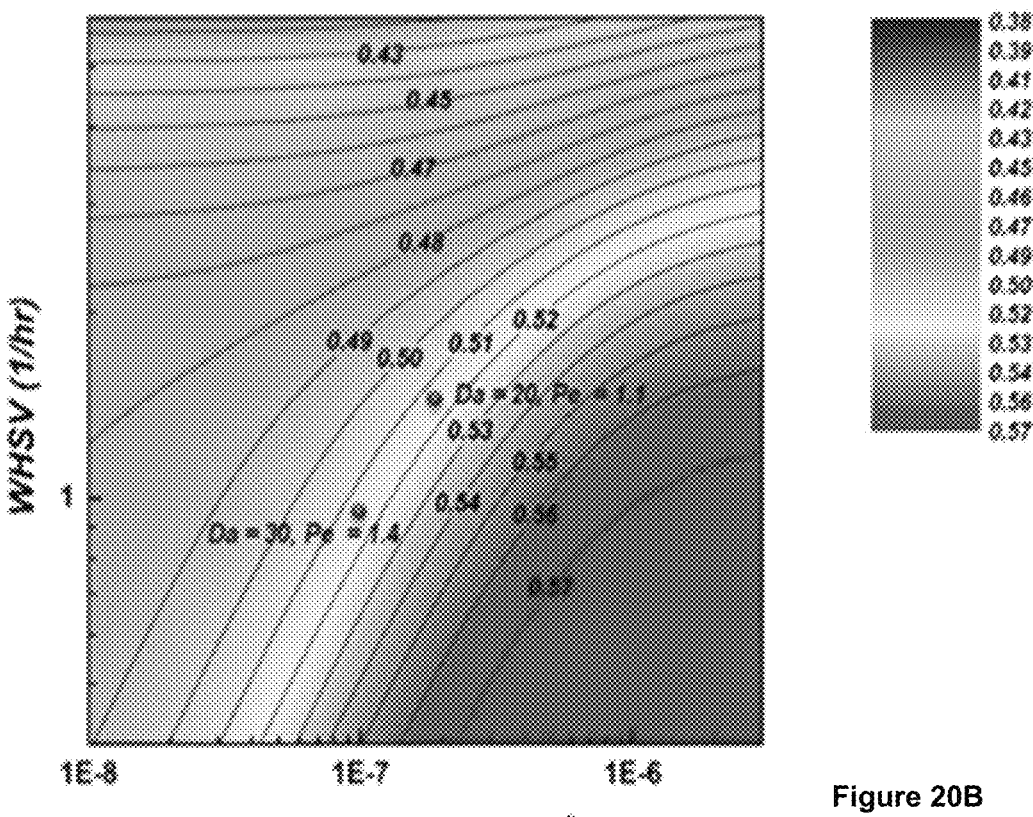
FIG. 20B is a graph showing WHSV as a function of permeance for a catalyst system in accordance with the disclosure.
Figure 21A:
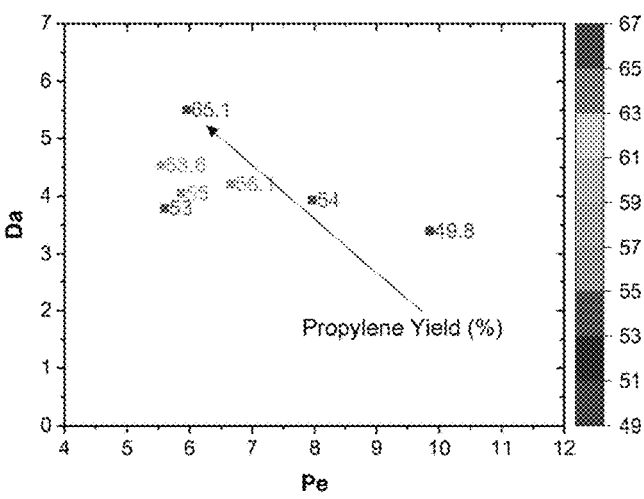
FIGS. 21A to 21C are graphs illustrating that a tubular membrane showed an about 3% improvement at 0.68 h$^{-1}$ and a sweep:feed ratio of 1:1 (higher area allowed for higher catalyst loading and operation at lower WHSV. Hollow fiber membrane in accordance with the disclosure showed an about 6% improvement at WHSV of 1.62 h$^{-1}$.
Figure 21B:
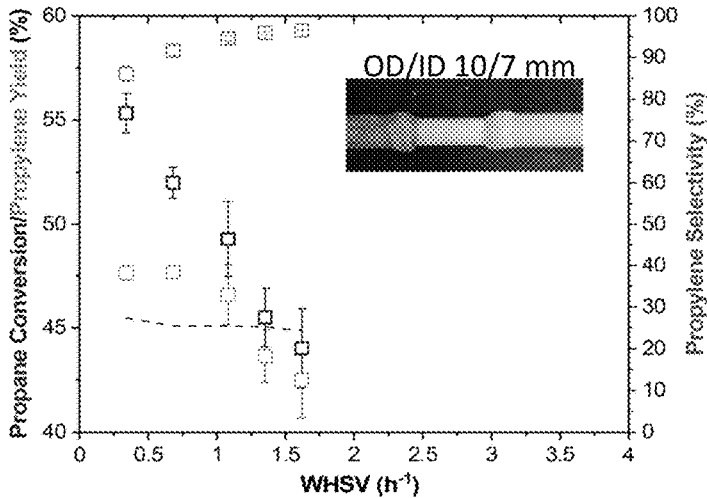
Figure 21C:
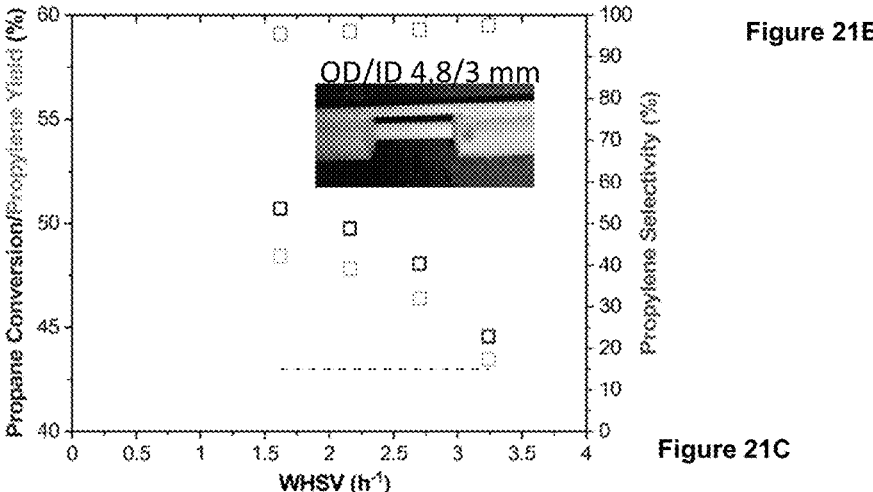
Figure 22A:
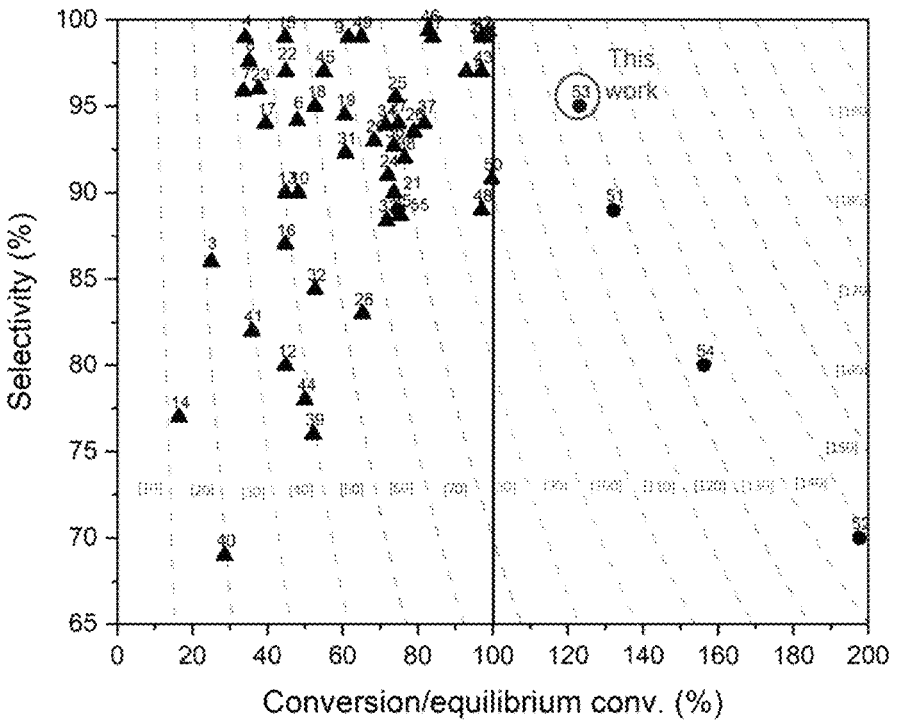
FIGS. 22A and 22B are graphs illustrating that coupling of the catalyst to a membrane reactor design in the catalyst system of the disclosure allowed for an improvement to about 117% propylene yield and a 95% propylene selectivity at 580° C.
Figure 22B:
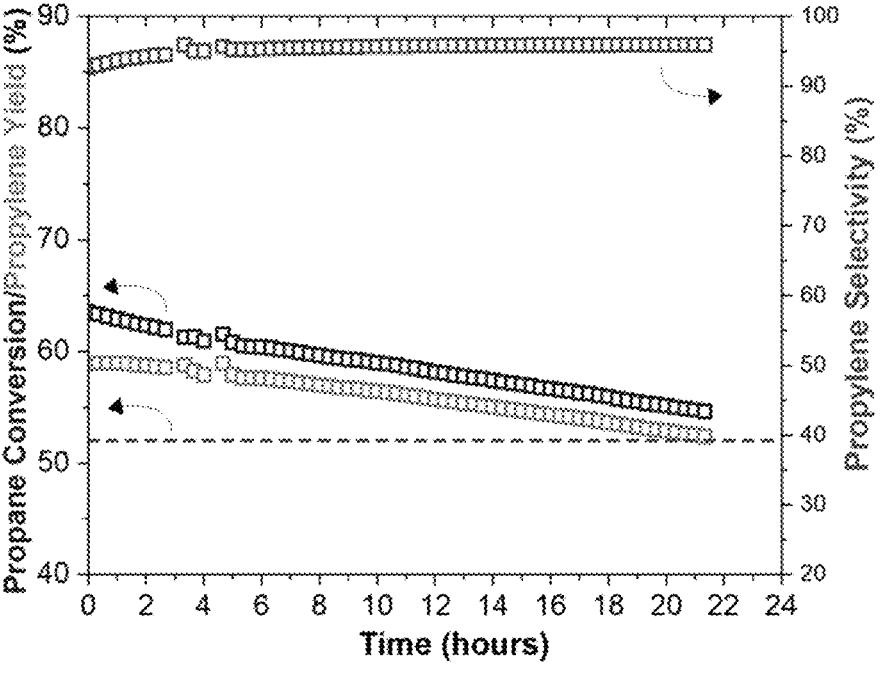
Figure 23A:
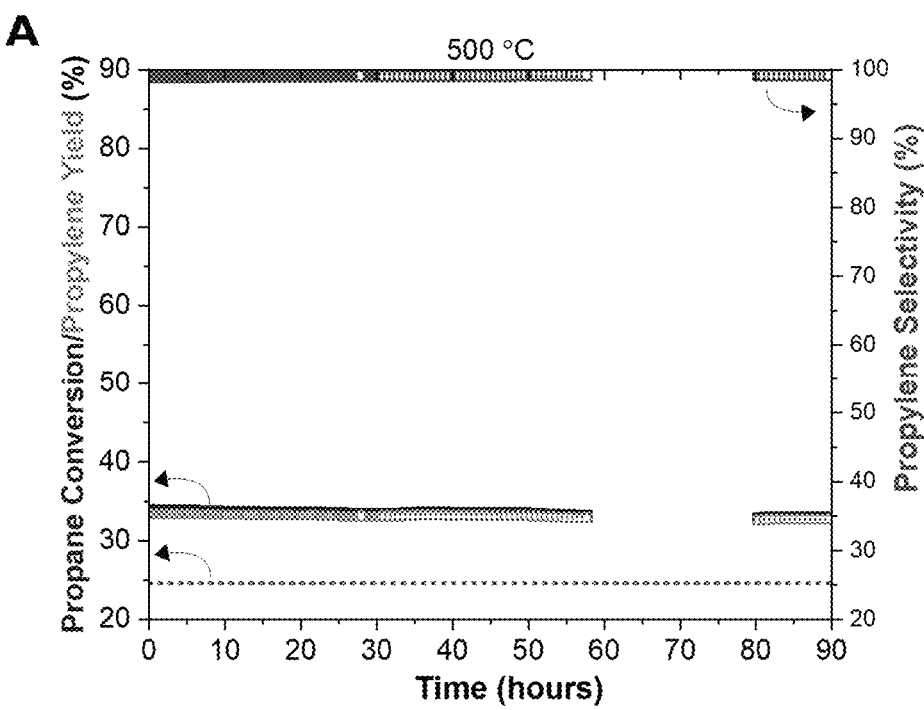
FIGS. 23A and 23B are graphs illustrating the lower thermodynamic propensity to form coke at lower temperatures. Faster deactivation in a membrane system can be avoided by operating at lower temperature (500° C.)
Figure 23B:
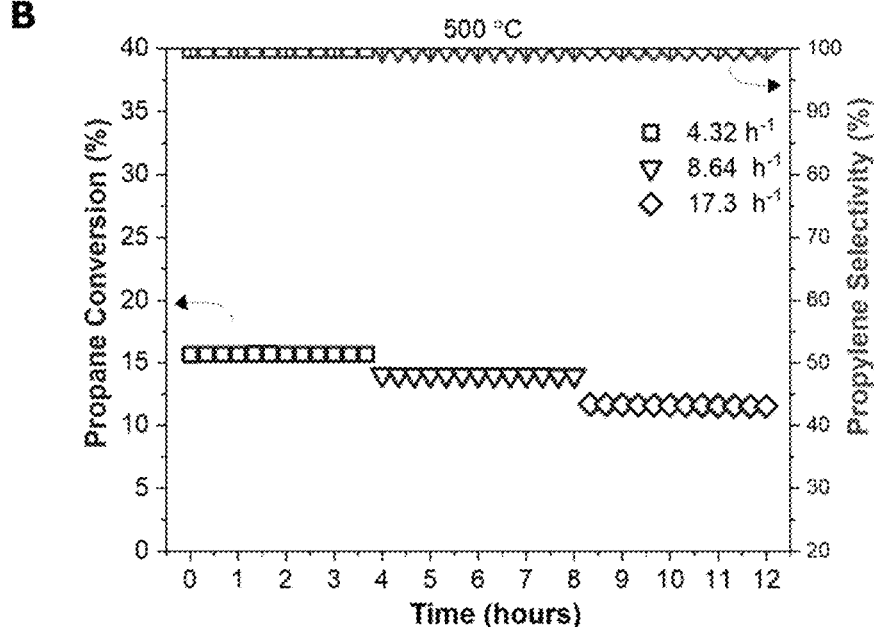

The catalyst system of the disclosure further beneficially can allow for operation at lower temperatures. For example, the catalyst system can operate for a dehydrogenation process at a temperature of about 400° C. to about 600° C. For example, the temperature can be about 400, 450, 500, 550, 600° C. and any ranges defined by such values and any values there between. The carbon-induced deactivation that occurs in dehydrogenation catalysis can be significantly limited by operating at lower temperatures. Additionally, lower temperature operation reduces energy input. In conventional systems, lower temperature would be expected to result in a decline in the propane equilibrium conversion. However, this was not observed in the catalyst systems of the disclosure. Without intending to be bound by theory, it is believed that the ability to operate at lower temperatures without sacrificing performance is achieved because the catalyst system is able to bypass the equilibrium limits as illustrated in FIG. 15.

Figure 5A:
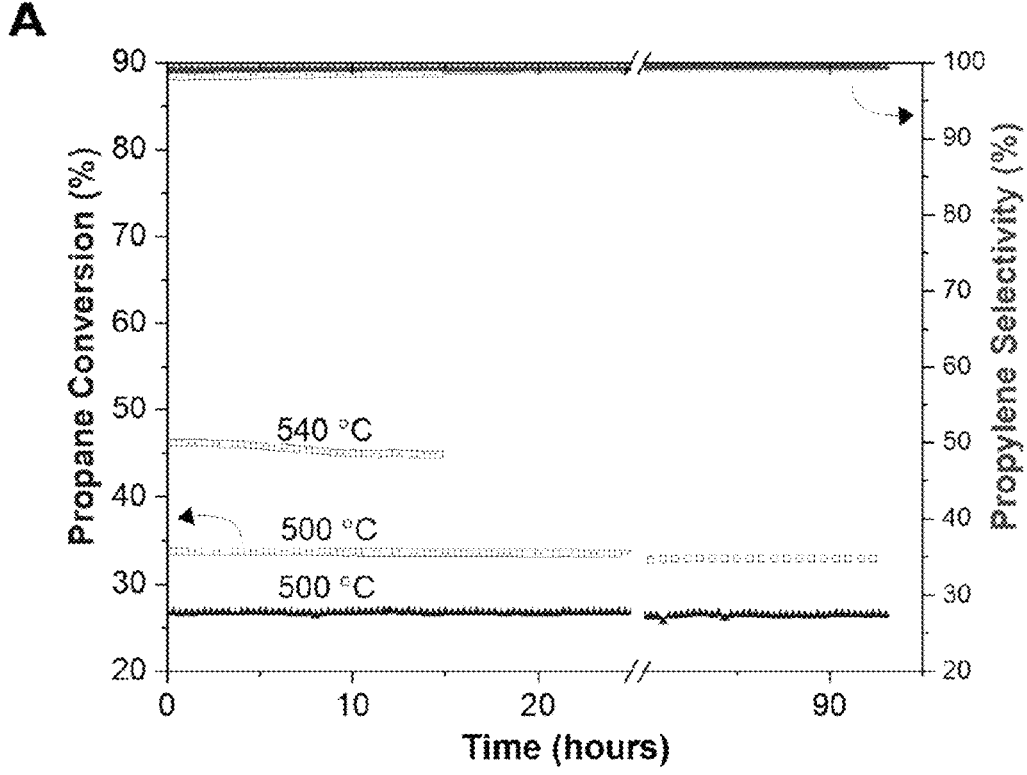
FIG. 5A is a graph showing propane conversion and propylene selectivity as a function of time for a catalyst system in accordance with the disclosure (squares) as compared to convention PBR (triangles). Reaction temperature was 500° C. or 540° C., $PC_{C3H8}$=1, WHSV=0.43 hours$^{-1}$ and sweep:feed ratio=10.

Successful lower temperature operation of the catalyst system is shown FIG. 5A, which shows the propane conversion and propylene selectivity as a function of time at 500° C. and 540° C. in a pure propane stream ((diluted by sweep gas backflow), a WHSV of 0.43 Wand a sweep:feed ratio of 10. Contrary to performance at 580° C., the system exhibited remarkable stability at these lower temperatures with >99% propylene selectivity. The operation of the catalyst system of the disclosure was compared to the performance of the same $Pt_1Sn_1/SiO_2$ catalyst operated in a packed bed reactor (PBR) under the thermodynamic equilibrium limit at 500° C., without the $H_2$ separating membrane, with the same amount of Ar as was present in the catalyst/membrane system. The data show that the catalyst system of the disclosure operates above the PBR performance by approximately 7 percent higher conversion without noticeable deactivation for more than 90 hours on stream. This improvement is equivalent to a 30° C. enhancement (temperature required to be able to operate a PBR at the same initial membrane system propane conversion).

Figure 5B:
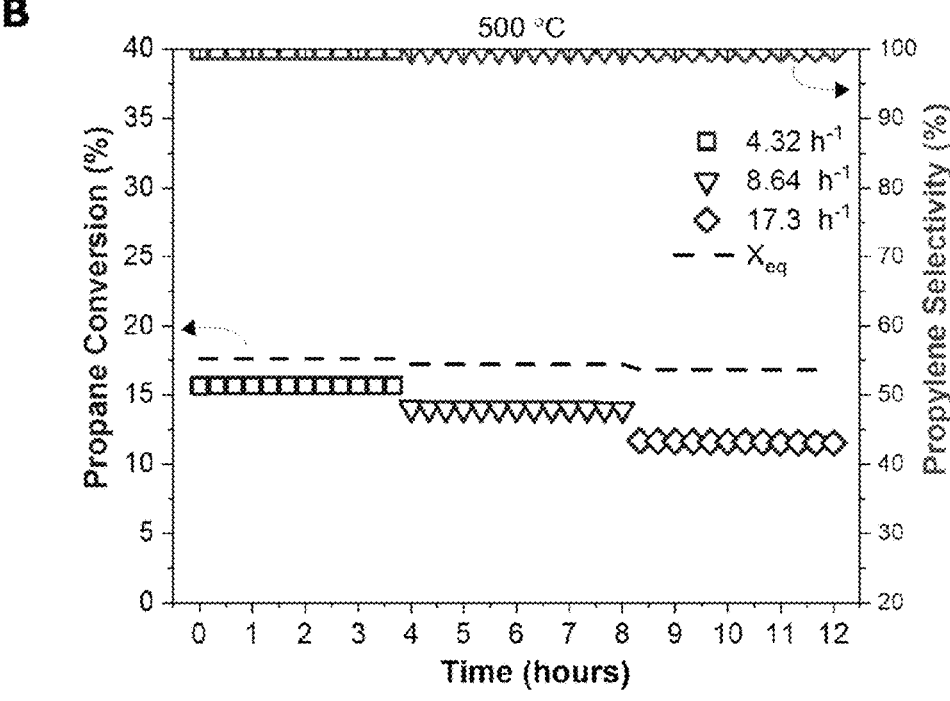
FIG. 5B is a graph showing propane conversion and propylene selectivity as a function time for a catalysts system in accordance with the disclosure at different WHSVs. Reaction temperature was 500° C., $P_{C3H8}$=1, and sweep flow rate=100 $cm^3$/min.

In FIG. 5B it can be seen that the catalyst system of the disclosure exhibits very stable performance even as the flow rates are significantly increased. These increased flow rates lead to lower conversions since the utilization of the catalysts is escalated under these conditions. At 500° C., the catalyst system of the disclosure was observed to be very stable with low deactivation rates at close to 100% selectivity to propylene

EXAMPLES

A catalyst system in accordance with the disclosure included an $Al_2O_3/Si_2$ hollow fiber membrane packed with a $Pi_1Sn_1/SiO_2$ PDH catalyst.

$H_2PtCl_6.6H_2O$ (>37.5% Pt, Sigma-Aldrich), $SnCl_2.2H_2O$ (reagent grade, Sigma-Aldrich), silica gel (high purity, pore size 60 Å, Sigma-Aldrich) were used for catalyst synthesis. Porous $\alpha-Al_2O_3$ ceramic hollow fiber (20 nm pore size) membranes on tubular supports of asymmetric structure (4.8 mm outer diameter (OD) and 3 mm inner diameter (ID)) from Coorstek have been used as supports. Tetraethyl orthosilicate (TEOS, Sigma-Aldrich, 99.9%) was used as a precursor for silica deposition. All materials were used as received without further purification.

$Pt_1Sn_1/SiO_2$ catalysts were synthesized using incipient wetness impregnation. The catalyst is fabricated by mixing chloroplatinic acid ($H_2PtCl_6$) and tin (II) chloride ($SnCl_2$) in 0.1 M hydrochloric acid solution to form a heterometallic Pt—Sn coordination complex such that the final weight percentages of Pt and Sn were 1 and 0.6 wt % (atomic ratio was 1:1). This solution was used to impregnate the $SiO_2$ support and obtain small Pt—Sn nanoparticles (between 1 and 2 nm in diameter) upon the reduction. After impregnation, the catalyst was dried overnight at 80° C. Detailed synthesis procedures have been reported previously in A. H. Motagamwala, R. Almallahi, J. Wortman, V. O. Igenegbai, S. Linic, Stable and selective catalysts for propane dehydrogenation operating at thermodynamic limit. Science 373, 217 (2021). Extensive catalyst characterization was also previously performed, showing its unique features of mixing of Sn and Pt atoms in the PtSn nanoparticles, small size of the nanoparticles (1-2 nm), and the stability against the separation of Sn from Pt on the $SiO_2$ support.

The membrane included a porous $Al_2O_3$ tube that had an outer diameter of about 4.8 mm and a thickness of about 0.9 mm. The tube consisted of two layers: an outer layer of ·860 micrometers (μm) with a 200 nm average pore size distribution, and an inner ~10 μm layer with a 20 nm average pore size distribution. The tube was formed by first cutting an alumina hollow fiber was cut into smaller sections (4 cm) using a diamond saw. Next, a fiber section was connected to two non-porous alumina tubes at both ends and sealed with a combination of ceramic and glass sealants. Alumina rods were attached on the non-porous tubes as supplemental support to the fiber and alumina tubes, to prevent mechanical stresses from resulting in any breakage. The sealed fiber/tubes system was placed in a furnace and heated to 900° C. at 1° C./min in flowing air to cure the seal, and then cooled to the silica deposition temperature of 600° C. at 1° C./min. The non-porous alumina tubes used as additional support has a 12.7 mm OD.

Figure 6:
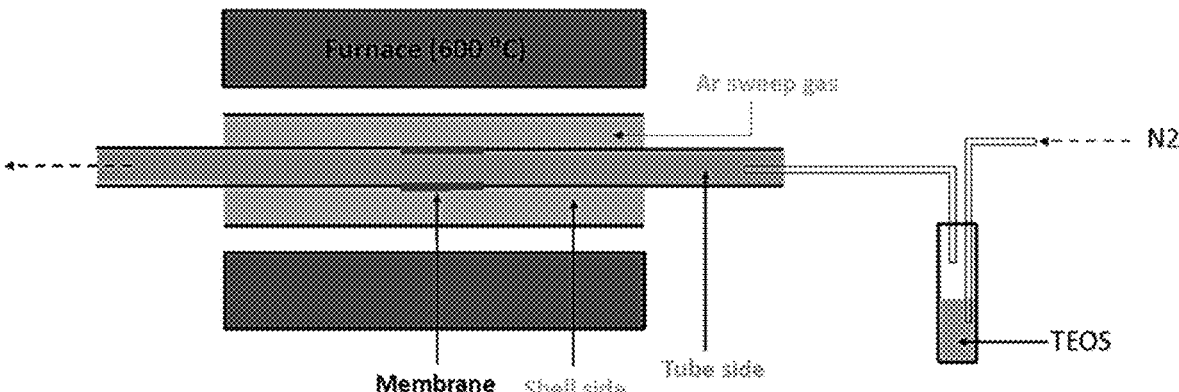
FIG. 6 is a schematic illustration of a TEOS CVD setup for $SiO_2$ deposition on $Al_2O_3$ hollow fiber membrane.
Figure 14:
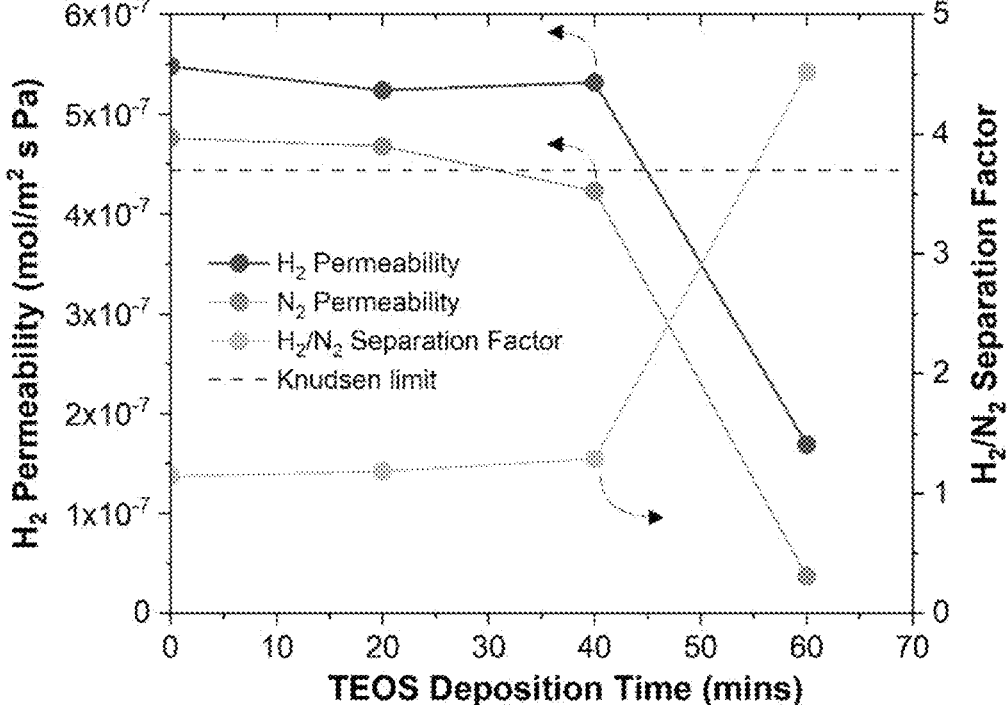
FIG. 14 is a graph showing $H_2$ permeability and $H_2/N_2$ separation factor (compared to the Knudsen separation limit) as a function of TEOS deposition time.

$SiO_2$ was deposited on the inner side of the $Al_2O_3$ tube through chemical vapor deposition (CVD) of tetraethyl orthosilicate (TEOS) at 600° C. The deposition process was conducted by placing two concentric tubes in a furnace as shown in FIG. 6. The hollow fiber connected to the non-porous alumina tubes was placed inside an outer tube formed of a quartz tube having a 17 mm inner diameter. A thin $SiO_2$ layer was deposited by a chemical vapor deposition (CVD) method where thermal decomposition of TEOS at a high temperature results in the $SiO_2$ layer on the $Al_2O_3$ substrate. After reaching the deposition temperature of 600° C., 40 $cm^3$/min of argon (Ar) gas was introduced on the outer, shell side of the tube, and 100 $cm^3$/min of nitrogen gas was passed through a bubbler filled with TEOS at room temperature and introduced to the inner tube side. The deposition time was varied until separation factors (measured using the shell side outlet gas composition obtained by the GC) at Knudsen limits were obtained (FIG. 14). The CVD process was paused at various times and the permeance of $H_2$ and $N_2$ were measured at different deposition times at 600° C.

After silica deposition, the reactor furnace was cooled to room temperature to pack the catalyst in the hollow fiber membrane, along its entire active length. Approximately 250 mg of the $Pt_1Sn_1/SiO_2$ PDH catalyst was packed inside the hollow fiber membrane on the tube side (where propane is fed), along the entire length of the tube. On the other side of the tube (shell side), an inert Ar sweep gas was used to carry the separated $H_2$. The $SiO_2/Al_2O_3$ membrane allows for some diffusion (backflow) of Ar to the inner tube side, and this backflow-induced dilution of the reactive mixture was accounted for in the calculations of the equilibrium propane conversion.

Figure 7:
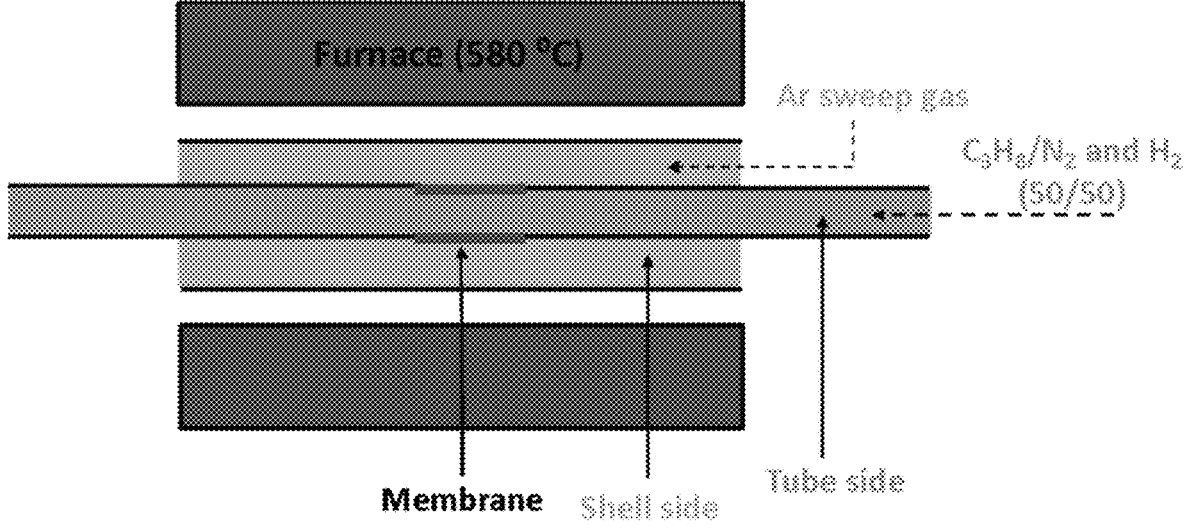
FIG. 7 is a schematic illustration of a gas permeation and reaction setup for $SiO_2/Al_2O_3$ hollow fiber membrane testing.
Figure 8:
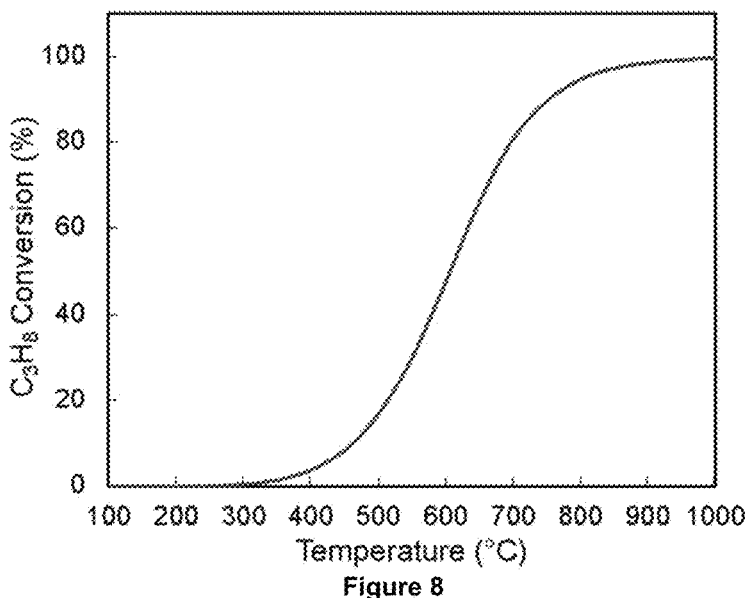
FIG. 8 is a graph showing equilibrium propane conversion as a function of reaction temperature for a pure undiluted propane stream.
Figure 9:
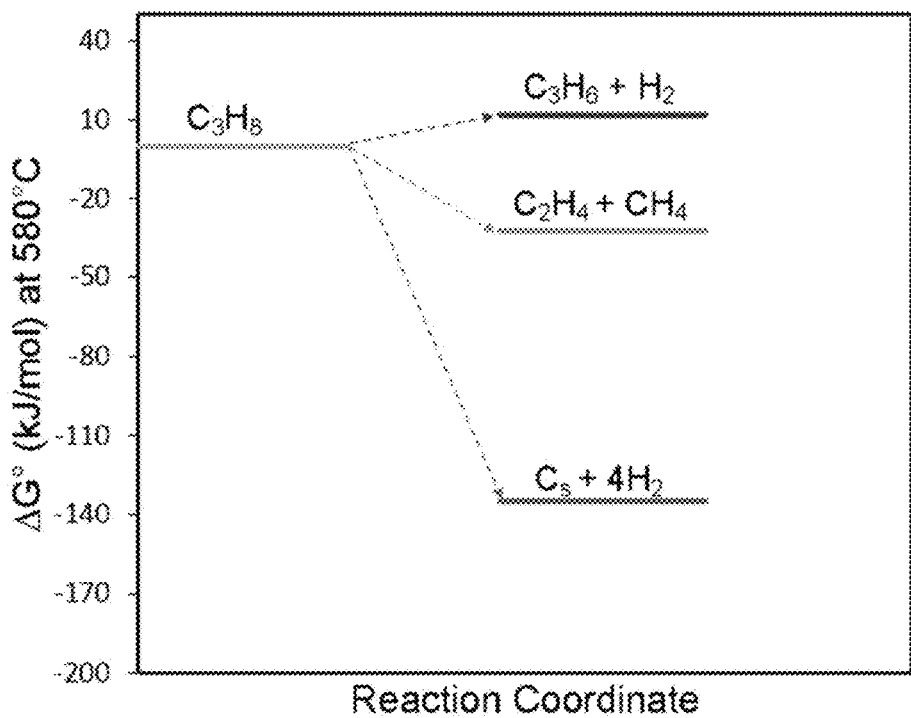
FIG. 9 is a graph showing the Gibbs free energy for propane dehydrogenation and side reactions at 580° C.

Propane dehydrogenation experiments were conducted in a packed-bed membrane reactor. The membrane setup consisted of two concentric tubes for a typical membrane tube and shell design (FIG. 7).

In a typical test, 250 mg catalyst was used. The catalyst bed was supported by quartz wool plug on either side. Once the catalyst was loaded in the reactor, the system was purged with $N_2$ (80 cm³/min) on the tube side and Ar (80 cm³/min) on the shell side. Following the purge, the gas composition on the tube side was changed to 20:80 $H_2$:$N_2$ (100 cm³/min) and the catalyst was heated at 2° C./min to 600° C. and held at 600° C. for 1 hour. Following the reduction at 600° C., the gas flow was switched to $N_2$ (100 cm³/min) and the reactor was cooled to the reaction temperature at 2° C./min. Once the reaction temperature was achieved, the inlet composition was changed to measure catalyst performance. The feed composition was 100 vol % $C_3H_8$. An Ar sweep gas was maintained on the shell side throughout the process in membrane experiments and was varied between 12-50 cm³/min during testing experiments to measure performance at different sweep-to-feed ratios. The propane feed flow was also varied for various WHSVs (based on propane flow) between 1-5 cm³/min in the packed-membrane reactor. The effluent from the reactor (tube and shell sides) was measured using the GC. The tube side products were used to calculate propane conversion, propylene selectivity, and propylene yield. The amount of Argon backflowing into the tube side was also monitored using the GC and accounted for as a diluent in the calculations of equilibrium conversion. The shell side products were used to calculate the $H_2$ removal rate. Both tube and shell side products were used to calculate the $H_2/C_3H_8$ separation factor.

The effectiveness of the $SiO_2/Al_2O_3$ hollow fiber membrane in separating $H_2$ was evaluated through a series of gas permeation and separation characterization experiments. It is desirable to have a membrane that can reach Knudsen separation limits. A study of $H_2$ separation from an equimolar $H_2/N_2$ mixture was performed by measuring the $H_2$ permeance and the $H_2/N_2$ separation factors as a function of TEOS deposition time. The deposition time is proportional to the amount of $SiO_2$ deposited and the thickness of the $SiO_2$ separating layer (FIG. 14). In these studies, TEOS deposition was performed until the $H_2/N_2$ separation factor (eq 2) was measured to be close to the Knudsen-separation limit (3.7 for $H_2/N_2$ separation (eq 3)). It was measured that for the $SiO_2$ layer thickness required to reach the $H_2/N_2$ Knudsen separation limits, the $H_2$ permeability through the membrane was relatively high at $>1.10^{-7}$ mol/m² s Pa for an equimolar mixture of $H_2/N_2$ with a total flow rate of 80 cm³/min and a sweep:feed ratio of 0.5. The sweep rate was the rate at which the Ar inert gas is moved on the shell side, removing gases that permeate through the membrane.

Figure 2A:
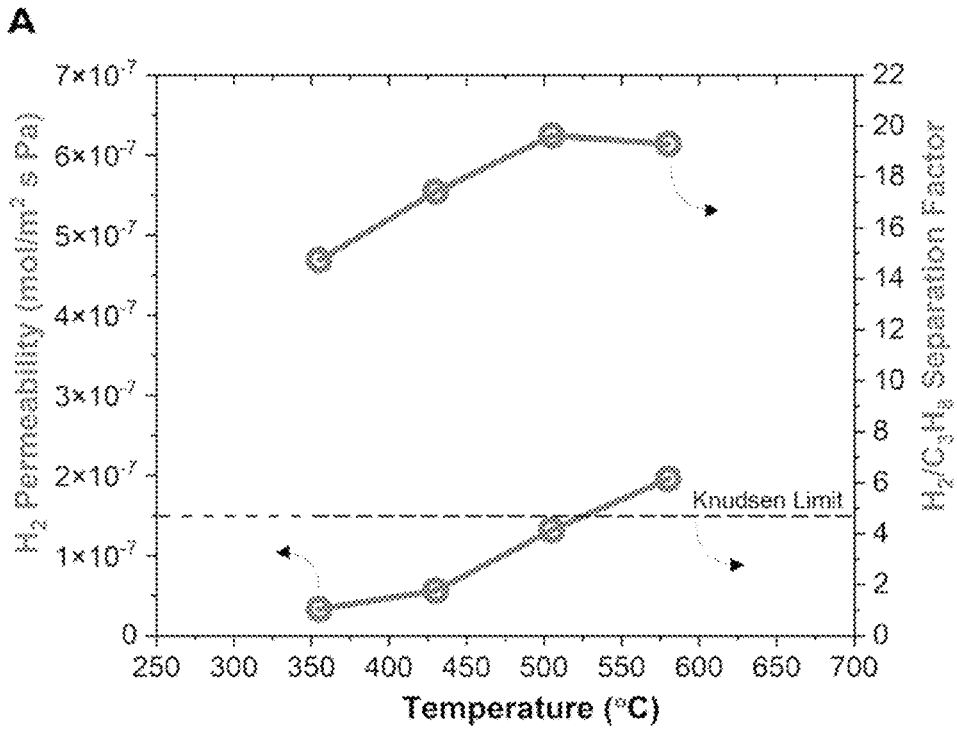
FIG. 2A is a graph showing $H_2$ permeability and $H_2/C_3H_8$ separation factor as a function of temperature for a hollow fiber membrane in accordance with the disclosure.
Figure 2B:
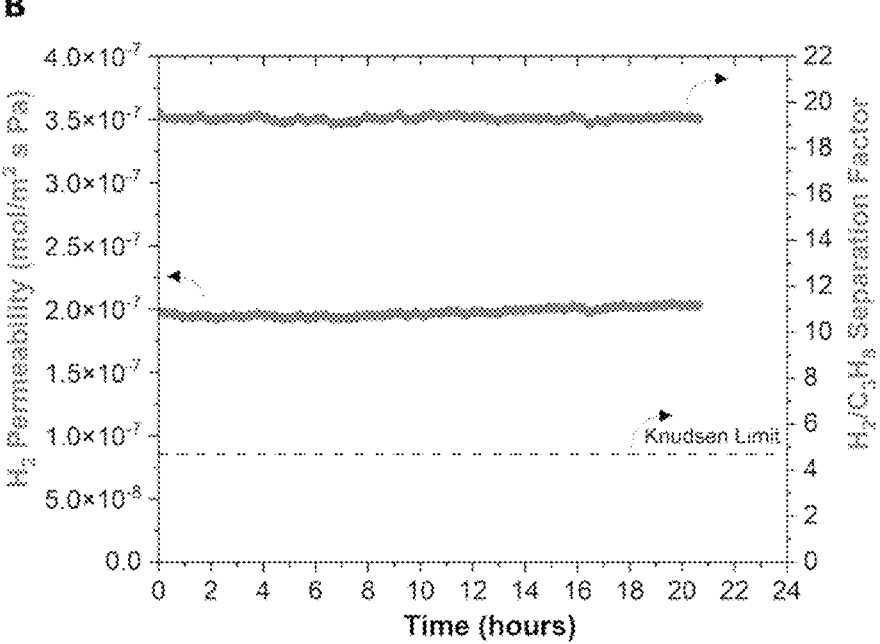
FIG. 2B is a graph showing $H_2$ permeability and $H_2/C_3H_8$ separation factor as a function of time for an equimolar mixture of $H_2$ and $C_3H_5$ (5 $cm^3$/min each) and an Ar sweep on the shell side (60 $cm^3$/min)
Figure 2C:
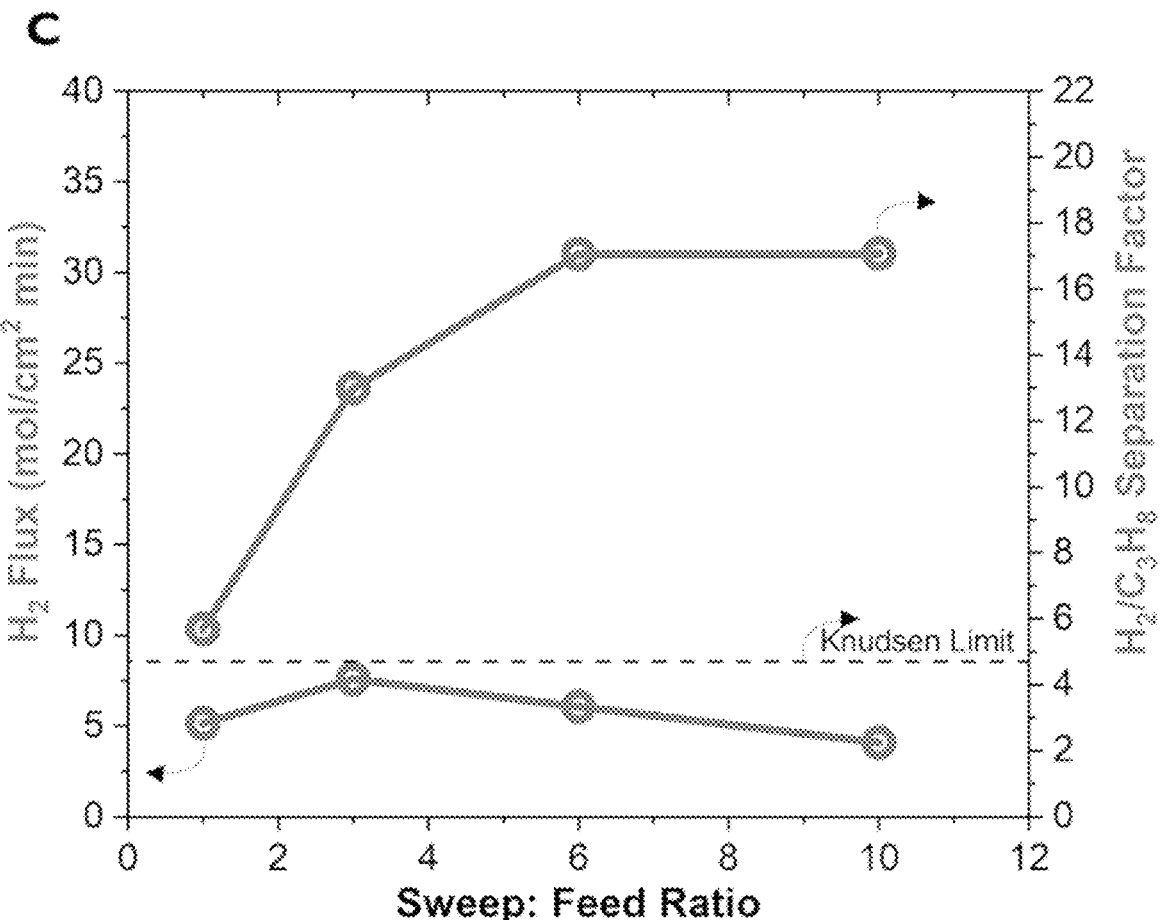
FIG. 2C is a graph showing $H_2$ flux and $H_2/C_3H_8$ separation factor as a function of sweep:feed ratios (Ar sweep varied between 10-100 $cm^3$/min on the shell side) at T=580° C.

Data in FIG. 2 show the performance of the $SiO_2$ based membrane in the context of the $H_2/N_2$ Knudsen separation, in separating $H_2/C_3H_8$ mixtures. Data in FIG. 2A show the $H_2$ permeability and the $H_2/C_3H_8$ separation factors measured at a total flow rate of 10 cm³/min of an equimolar mixture of $H_2$ and $C_3H_8$ at a sweep:feed ratio of 6. At 580° C., where PDH is often operated, the $SiO_2/Al_2O_3$ hollow fiber membrane exhibited a $H_2$ permeability of ~2.10⁻⁷ mol/m²s Pa and a $H_2/C_3H_8$ separation factor of 19. The data in FIG. 2B show the membrane performance was stable over time with no performance degradation over the duration of the study of ~20 hrs. The data in FIG. 2C show higher separation factors at higher sweep:feed ratios, even exceeding the Knudsen limit. This high separation factors can be attributed to higher sweep-induced change to the driving force to diffuse $H_2$ through the membrane compared to the driving force to diffuse propane, i.e., the partial pressure of $H_2$ ($P_{H2}$) is lowered on the shell side by increasing the sweep gas flow rate. It was also found that increasing the sweep: feed ratio above 6 did not lead to further increases in the separation factors.

Figure 3A:
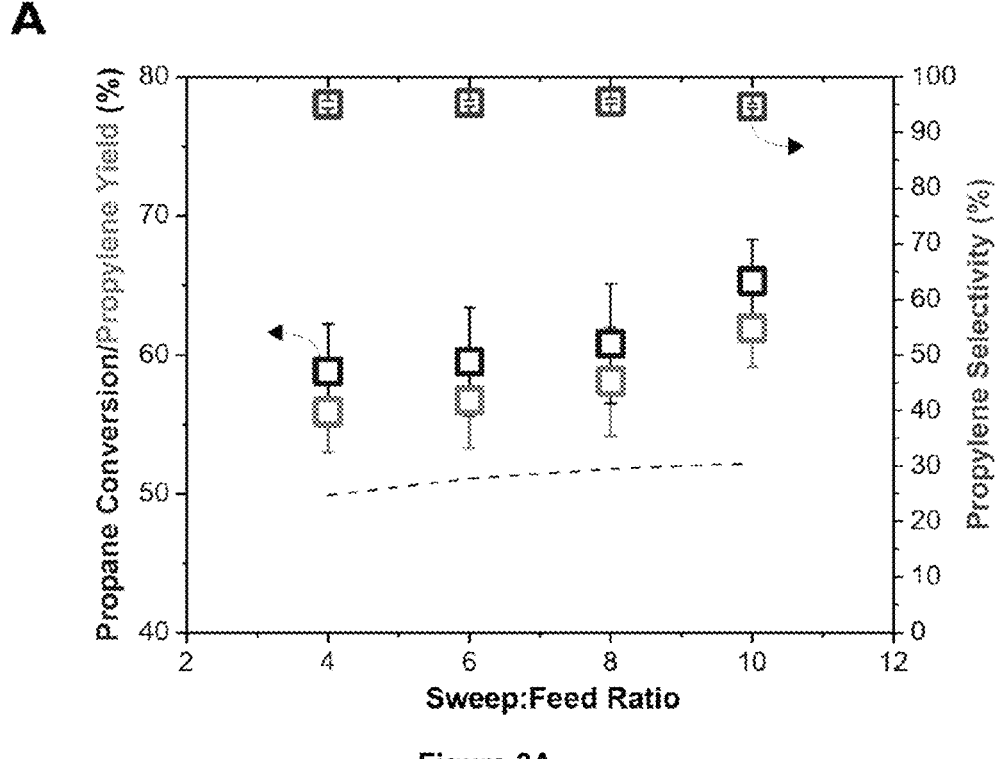
FIG. 3A is a graph showing propane conversion, propylene selectivity and propylene yield as a function of sweep:feed ratios (WHSV=1.3 hours$^{-1}$) compared to reaction equilibrium limit (dashed line) calculated for the same experimental conditions.

Data in FIG. 3A show the performance of the catalyst system in propane dehydrogenation at 580° C., measured at pure propane feed (diluted by Ar backflow discussed above), sweep:feed ratios between 4-10 and a constant weight hourly space velocity (WHSV) of 1.3 h⁻¹. WHSV is defined as the mass of propane entering the reactor per unit time divided by the mass of the catalyst in the reactor. The different sweep:feed ratios were obtained by varying the Ar sweep gas flow rate on the shell side between 12-50 cm³/min to increase selective separation as described earlier. It was observed that the thermodynamic limit on propane conversion under these reaction conditions (dashed black line) was 50-52%, depending on the amount of Ar diluent present at the different sweep:feed ratios. At these conditions, the catalyst system reached propane conversions up to 10% higher than the equilibrium conversion with >95% propylene selectivity.

Figure 3B:
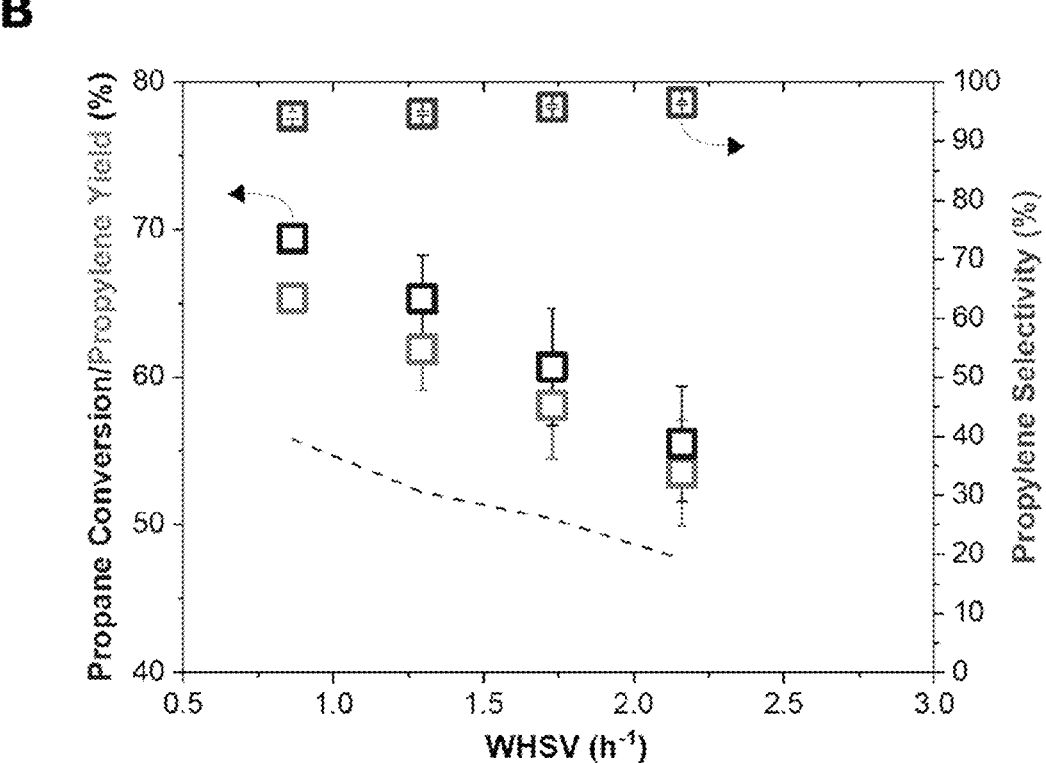
FIG. 3B is a graph showing propane conversion, propylene selectivity, and propylene yield as a function of WHSV (sweep:feed=10) compared to reaction equilibrium limit (dashed line) calculated for the same experimental conditions.

Another parameter that can be tuned to improve the $H_2$ removal rate is the WHSV, since at higher gas residence times (as the WHSV is lowered), a membrane can remove higher fractions of $H_2$ produced during the reaction. Data in FIG. 3B show the performance of the catalyst/membrane system for propane dehydrogenation at 580° C., pure propane feed (diluted by Ar backflow), a constant sweep:feed ratio of 10, and with WHSVs changing between 0.86-2.16 h⁻¹. The different WHSVs were obtained by varying the propane flow rate on the tube side between 2-5 cm³/min for a constant catalyst loading of 250 mg. It was observed that as WHSV is decreased, propane conversion is significantly increased without sacrificing the product selectivity. The changes in the limiting, equilibrium conversion (dashed line in FIGS. 3A and B) are due to the different levels of Ar backflow at different conditions.

Figure 3C:
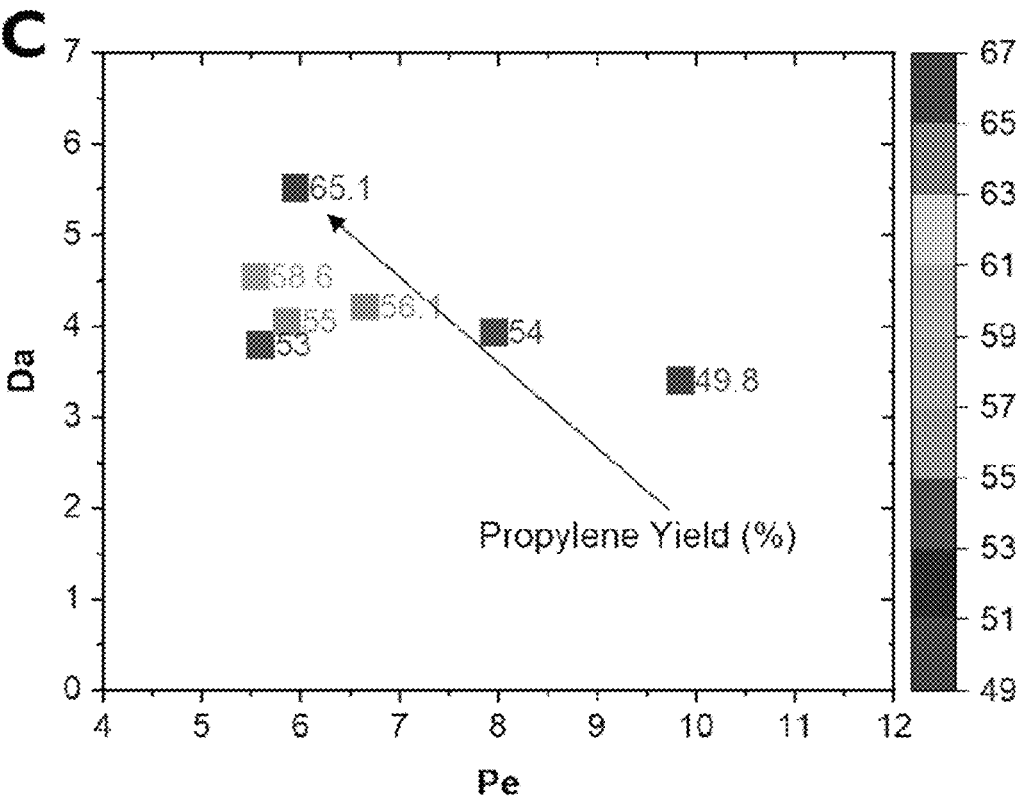
FIG. 3C is a graph showing propylene yield as a function of dimensionless Da and Pe.
Figure 3D:
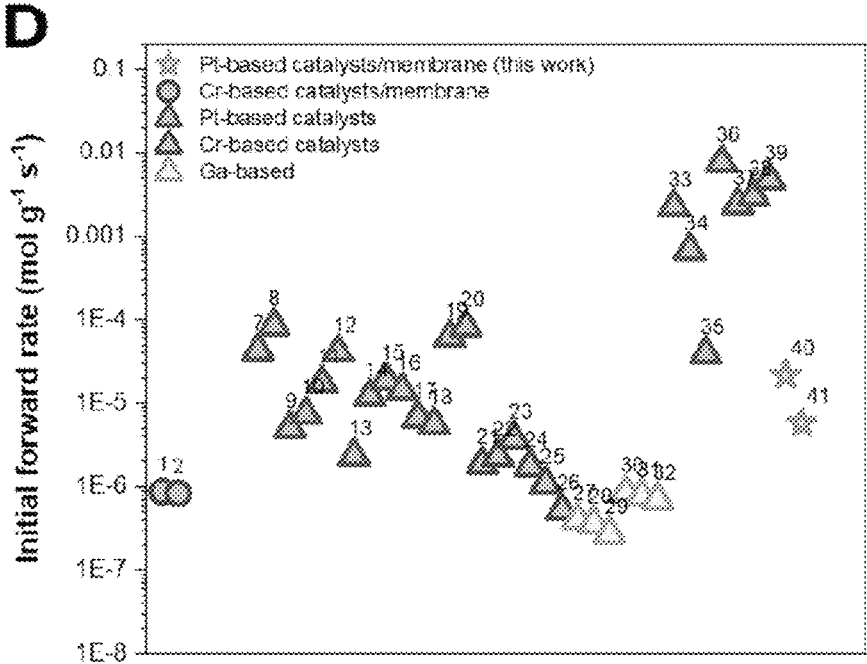
FIG. 3D is a graph showing initial reaction rate for various catalysts systems in accordance with the disclosure and PBR catalysts reported in the literature, points 40 and 41 580 and 500° C.) represent the catalyst system of the disclosure. Numbers in the figure correspond to row number in Table 2.
Figure 3E:
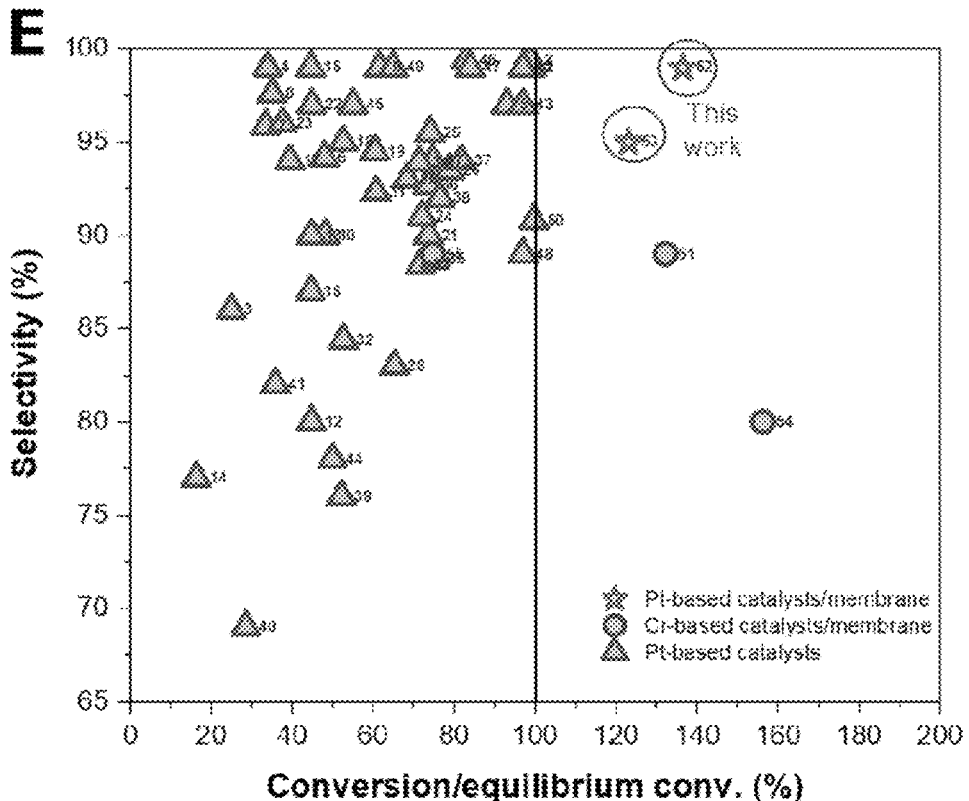
FIG. 3E is a graph showing conversion-selectivity plots for different PDH catalysts. Numbers in the figure correspond to row number in Table 1.

Data in FIG. 3C show propylene yield in the catalyst system as a function of the two dimensionless numbers, Da and Pe (calculated using eq 7-8). That data was obtained at 580° C., using a pure propane stream. The Da and Pe numbers were varied by changing the WHSV and sweep: feed ratio covering the range of WHSVs between 0.86 and 2.16 h⁻¹ and sweep:feed ratios of 4-10. The partial $H_2$ pressure different across the membrane was changed by changing the sweep:feed ratio, therefore affecting the Pe number, while changing WHSV impacts both the Da and Pe numbers. The data in FIG. 3C show that an improved performance is seen at higher Da and lower Pe[27,29] and that at 580° C. the highest propylene yield of 65% was achieved, which is 10% above the equilibrium limit (assuming 100% selectivity to propylene) of 55%. Based on these analysis, it was concluded that for the hollow fiber catalyst/membrane tubular geometries analyzed herein, at 580° C. the enhancement factors in propylene yield and conversion of approximately 10% compared to the equilibrium conversion (from 55 to 65% conversion increase) beyond that observed in the present testing is possible.

Characterization

Figure 1F:
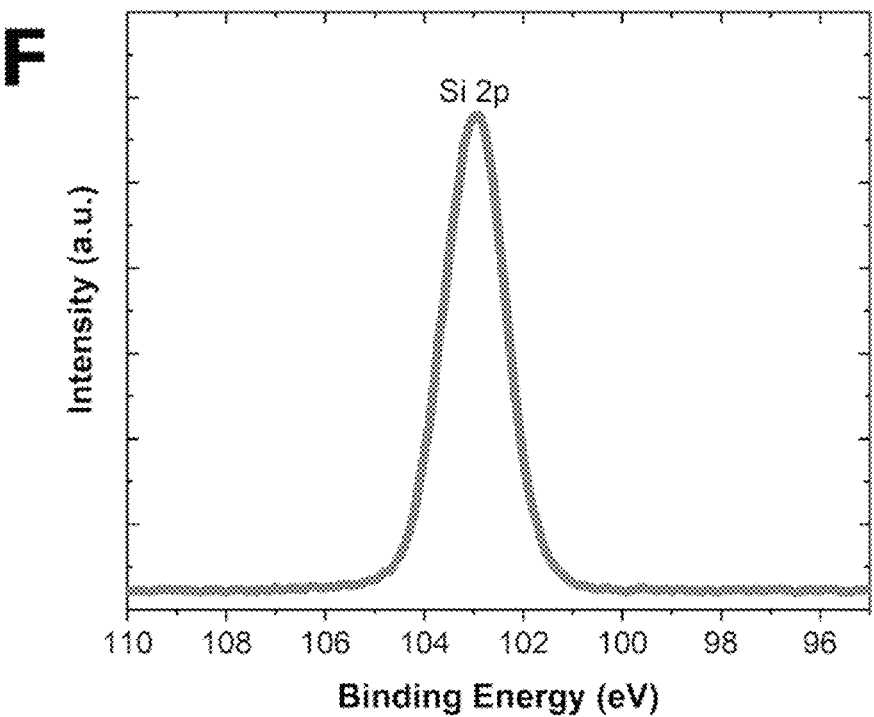
FIG. 1F is a graph showing the Si 2 p photoemission spectra of an $SiO_2/Al_2O_3$ hollow fiber membrane in accordance with the disclosure.
Figure 1G:
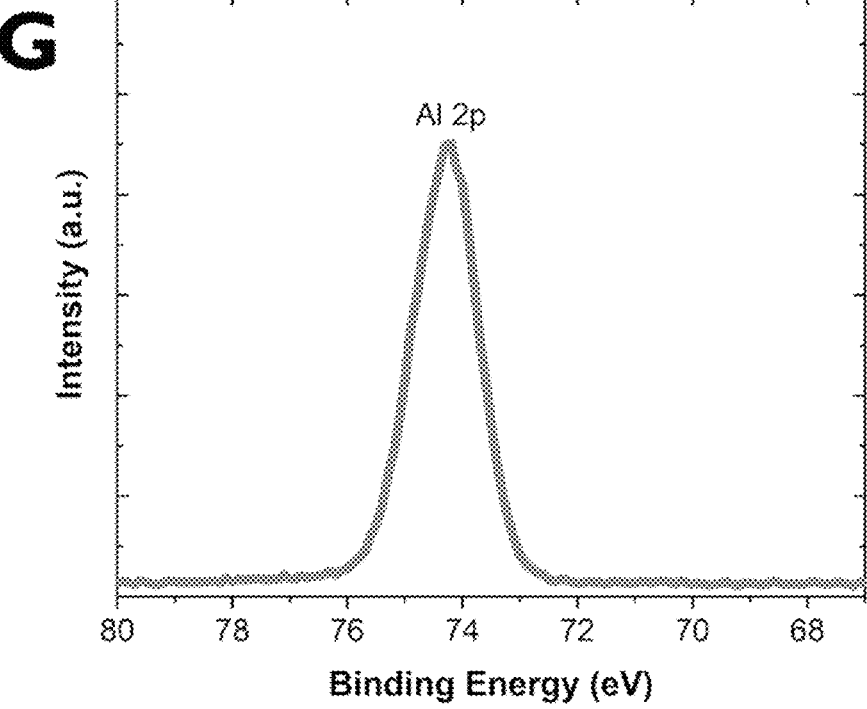
FIG. 1G is a graph showing the Al 2 p photoemission spectra of an uncoated $Al_2O_3$ hollow fiber membrane.
Figure 11:
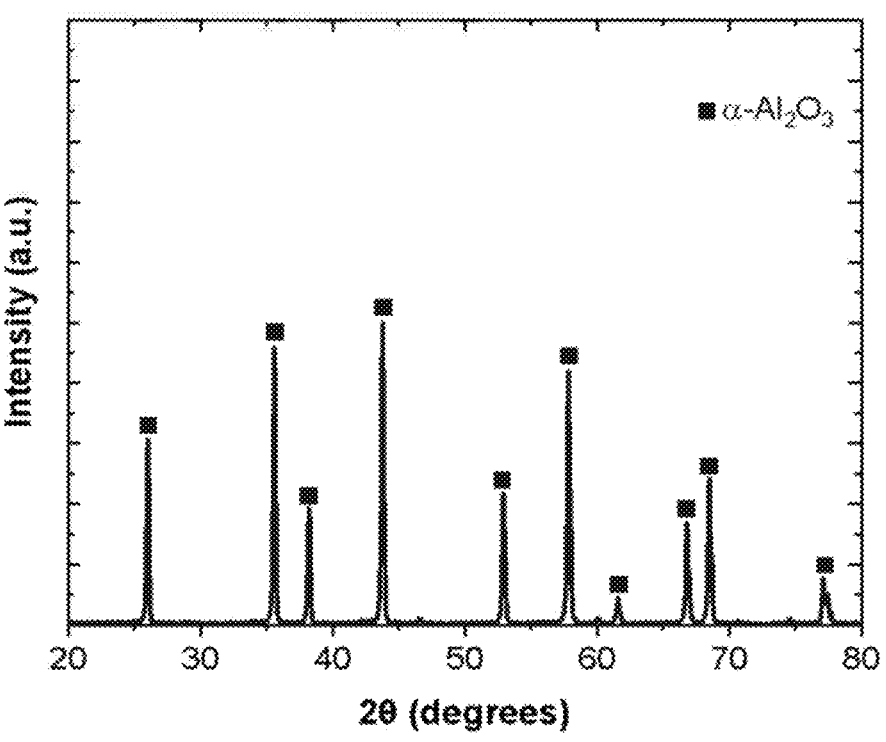
FIG. 11 is a graph showing the X-ray diffraction pattern for $SiO_2/Al_2O_3$
Figure 12:
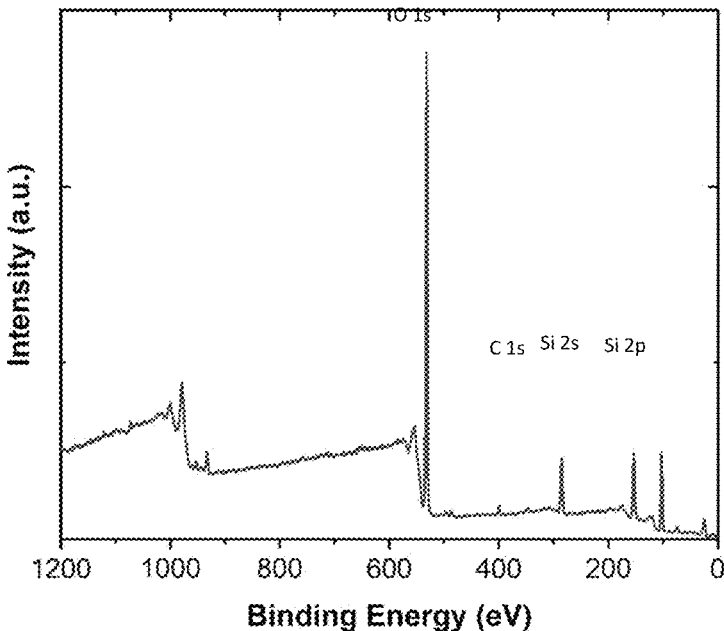
FIG. 12 is a graph showing survey photoemissions of an $SiO_3$ coated $Al_2O_3$ membrane.
Figure 13:
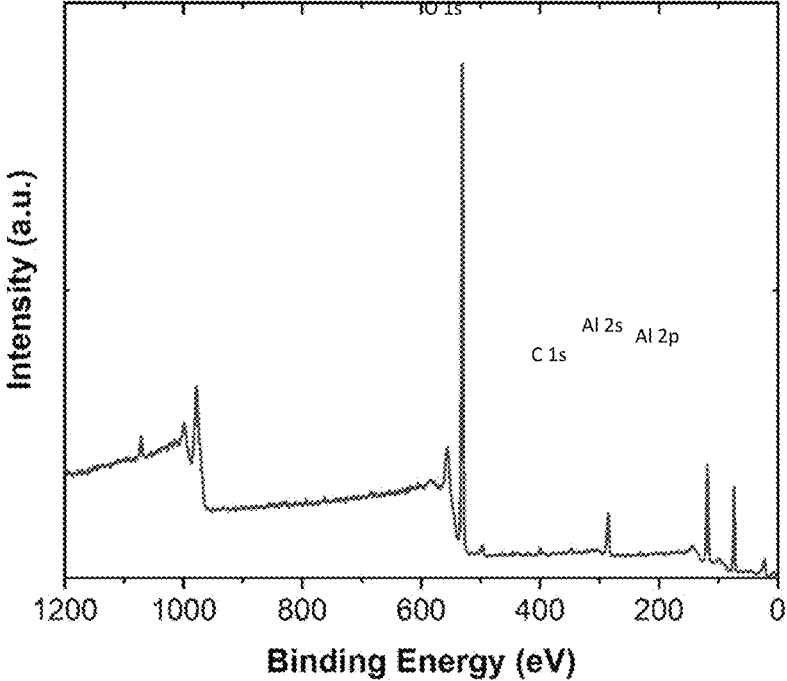
FIG. 13 is a graph showing survey photoemissions spectral of an uncoated $Al_2O_3$ membrane.

The deposition resulted in the formation of a thin $SiO_2$ separation layer on the inner side of the $Al_2O_3$ tube as shown in the cross-section image in FIG. 1D. The $SiO_2$ separation layer was formed to a thickness of about 500 nm. The deposited $SiO_2$ covered the entire inner surface of the porous $Al_2O_3$ tube. This was confirmed by SEM imaging as shown in FIG. 1E. Referring to FIG. 1E, it can be seen that the $SiO_2$ separation layer was a smooth layer with very small pore size distribution and no pin holes or cracks. The complete coverage of the $Al_2O_3$ inner surface with the $SiO_2$ separation layer was also confirmed using x-ray photoelectron spectroscopy (XPS). FIGS. 1F and 1G show the XPS spectra associated with the characteristic Si 2 p and Al 2 p peaks for the $SiO_2$ coated and uncoated $Al_2O_3$ tubes, respectively, showing that no Al peaks were detected for the $SiO_2$ coated sample. FIG. 11 is an X-ray diffraction patter for the membrane, but only shows the spectra for the $Al_2O_3$ substrate since the topmost $SiO_2$ layer is amorphous. FIGS. 12-13 show survey photoemission spectra of the coated and uncoated samples respectively.

X-ray diffraction (XRD) was used to confirm the $Al_2O_3$ crystalline phases in the hollow fiber membranes. XRD data was collected using Rigaku MiniFlex 600 (Cu Kα source, λ=1.54059 Å) with a tube voltage of 40 kV and a current of 15 mA. A continuous scan mode was used to collect 2Θ data with a step size of 0.02° and speed of 2°/min.

Samples of the alumina support substrate and silica-coated membrane were characterized using a scanning electron microscope (Tescan MIRA3). The samples were prepared by mechanically breaking the membranes and sputter-coating them with gold before loading them into the microscope. Morphologies and layer thicknesses were evaluated at a 12 kV accelerating voltage. The cross-section image (FIG. 1D) was obtained using focused ion-beam milling (FIB) on a TFS Nova 200 Nanolab with an accelerating voltage of 5 kV.

X-ray photoelectron spectroscopy (XPS) was performed to determine the surface composition of $SiO_2$-coated and uncoated $Al_2O_3$ membrane samples. XPS data was taken using a Kratos Axis Ultra XPS with a monochromated alumina Kα source operating at 8 mA and 14 kV. Regional Si 2 p and Al 2 p scans were acquired using 5 sweeps with a dwell time of 60 seconds. In all experiments, the charge neutralizer was used to prevent charging of the samples, and the carbon 1s peak at 285 eV was used to detect any shifting of the spectrum.

Gas Permeation Measurements

Gas permeation measurements were conducted in the previously described setup (FIG. 7) and in the temperature range of 355-580° C., by flowing an equimolar mixture of $H_2$ and $C_3H_8$ at atmospheric pressure in the inner tube and varying flow rates of Ar as a sweep gas on the outer shell side to carry the permeating gases. The driving force for the $H_2$ transport through the membrane is created by using an inert (Ar) sweep gas in a co-current mode. Various flow rates and sweep-to-feed ratios were investigated. All gas flow rates were controlled using mass flow controllers (Cole-Parmer), and the effluent gases from both the tube, shell, and combined tube/shell side effluents were analyzed by a gas chromatograph (Agilent 7890B GC) equipped with a flame ionization detector and two thermal conductivity detectors. Gas permeances were calculated using the outlet gas flow rate and the concentration of the permeated gas on the shell side obtained using the GC. The total pressure on both sides of the membrane was maintained at atmospheric pressure. The membrane permeance is defined as the gas flux through the membrane per unit surface area per the partial pressure difference (Equation 1).

$$\text{Permeance}\left(\frac{\text{mol}}{m^2 s \text{Pa}}\right) = \frac{y_i F_{shell}}{A \Delta P_i} \tag{1}$$

Where $y_i$ is the molar fraction of the permeating gas, $F_{shell}$ is the flow rate on the shell side, A is the effective membrane area of the hollow fiber, and $\Delta P_i$ is the partial pressure difference.

The separation factor is calculated from the molar fractions of the two gases in the permeate and retentate streams (Equation 2) and is compared to the Knudsen separation factor (Equation 3).

$$\text{Seperation Factor}_{A,B} = \frac{\frac{x_A}{x_B}}{\frac{y_A}{y_B}} \tag{2}$$

where $x_A$ and $x_B$ are the molar fractions of gases A and B in the permeate stream and $y_A$ and $y_B$ are the molar fractions of gases A and B in the retentate stream.

$$\text{Seperation Factor}_{Kn,A,B} = \sqrt{\frac{M_B}{M_A}} \tag{3}$$

where $M_i$ is the molar mass of gas i.

Calculations Based on Reaction Testing

Propane conversion was calculated on a carbon basis:

$$\text{Propane Conversion} = \frac{1 \times F_{CH_4} + 2 \times F_{C_2H_6} + 2 \times F_{C_2H_4} + 3 \times F_{C_3H_6}}{1 \times F_{CH_4} + 2 \times F_{C_2H_6} + 2 \times F_{C_2H_4} + 3 \times F_{C_3H_6} + 3 \times F_{C_3H_8}} \tag{4}$$

Propylene selectivity was also calculated on a carbon basis:

$$\text{Propylene selectivity} = \frac{3 \times F_{C_3H_6}}{1 \times F_{CH_4} + 2 \times F_{C_2H_6} + 2 \times F_{C_2H_4} + 3 \times F_{C_3H_6}} \tag{5}$$

Propylene yield:

Propylene yield=propane conversion×propylene selectivity (6)

Damkohler number:

$$Da = \frac{\text{initial reaction rate} \times MW_{C_3H_8}}{WHSV} \quad (7)$$

Peclet number:

$$Pe = \frac{WHSV \times \text{mass}_{cat}}{MW_{C_3H_8} \times \text{permeance} \times \text{membrane area}} \quad (8)$$

Catalyst System Operated with $O_2$ Flow

Figure 25A:
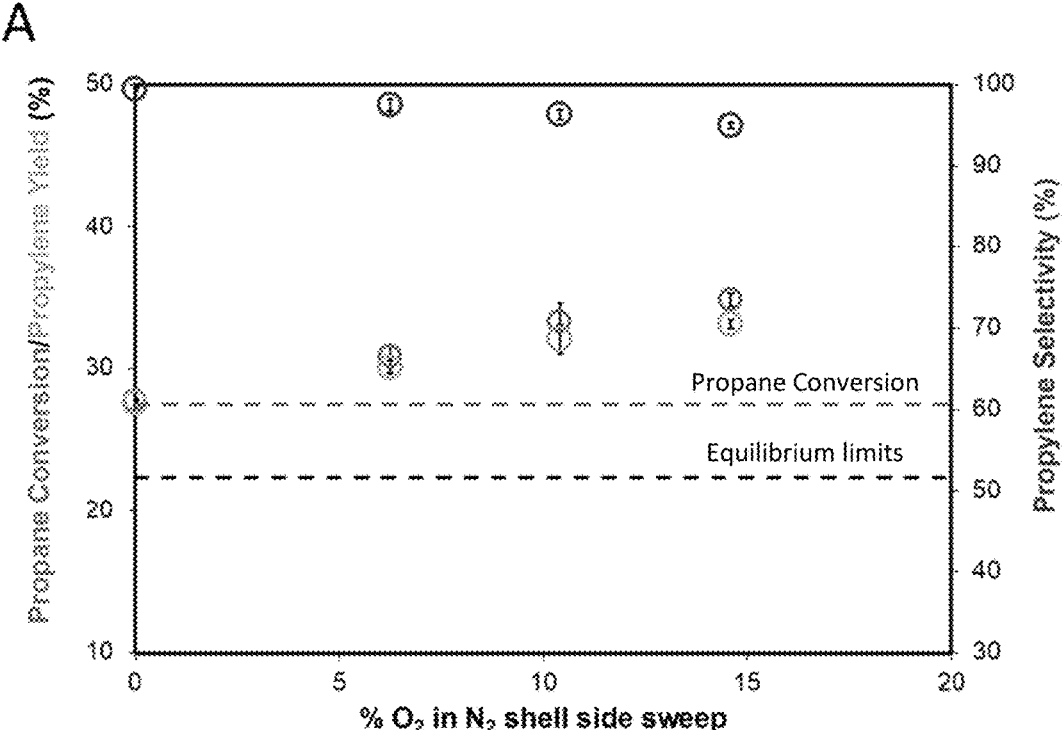
FIG. 25A is a graph showing propane conversion, propylene selectivity and propylene yield as a function of % $O_2$ introduced in the sweeping gas compared to reaction equilibrium limit (bottom dashed line) and the system with no $O_2$ (top dashed line)

A catalyst system in accordance with the disclosure was operated for PDH with a sweeping gas including 0-15% $O_2$ in the sweeping gas flow. Referring to FIG. 25A, the performance of the system in PDH at 500° C., measured for a pure propane feed (diluted by N2 backflow discussed above), sweep:feed ratio of 12 including 0-15% $O_2$ in the sweeping flow rate, and a constant weight hourly space velocity (WHSV) of 0.86 h−1 is shown. The total $N_2$ sweeping flow rate on the shell side was maintained at 24 cm$^3$/min to maintain a constant sweeping driving force even as different amounts of $O_2$ were introduced. WHSV is defined as the mass of propane flowing per unit time divided by the catalyst mass. The thermodynamic limit on propane conversion under these reaction conditions was also shown in FIG. 25A as being 22% based on the amount of $N_2$ backflow. A high sweep:feed ratio was used to promote higher selective $H_2$ permeation, because the $H_2$ partial pressure driving force is increased. By using the sweeping gas to remove permeated $H_2$ from the reaction zone, the reaction is shifted to the product side, and therefore, propane conversion was enhanced beyond traditional equilibrium limits imposed on the PDH reaction. The data show that at these conditions, before introducing $O_2$ in the $N_2$ sweep, the catalyst system reached a propane conversion up to 28%, which is 6% higher than equilibrium conversion with >99% propylene selectivity. Next, 6-15 vol % of $O_2$ was introduced in the $N_2$ sweeping gas on the shell side. As a result of this $O_2$ presence in the sweeping gas, higher propane conversions of 31-35% were obtained Without intending to be bound by theory, it is believed that these greater propane conversions are due to increasing $H_2$ removal levels because of the consumption of $H_2$ by $O_2$ in the oxidation reaction. However, this increase in propane conversion was associated with a slight decrease in propylene selectivity because of the emergence of carbon oxide ($CO_x$) products. Nonetheless, selectivity to propylene was still maintained above 95%. To account for this lower propylene selectivity, propylene yield was also calculated as the product of propane conversion and propylene selectivity. Propylene yield for the $O_2$ conditions was 3-6% above the no $O_2$ in sweep case, for a total of 8-11% above equilibrium limits.

Figure 25B:
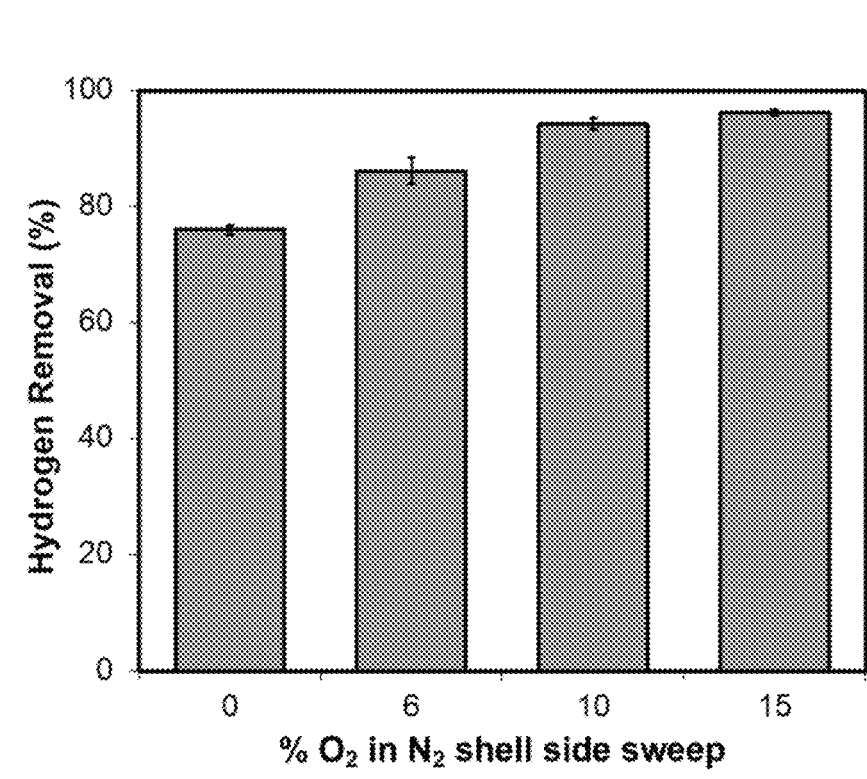
FIG. 25B is a graph showing precent $H_2$ removal as a function of % $O_2$ in the sweeping gas.

Referring to FIG. 25B, $H_2$ removal percentages for the catalyst system at the different amounts of $O_2$ in the inert sweeping gas are shown. $H_2$ removal was calculated by comparing the relative partial pressures of propylene and $H_2$ on the tube side, since the reaction stoichiometry for PDH with no $H_2$ removal stipulates equal amounts of both products. At 0% $O_2$ in the inert sweeping gas, the membrane was able to remove 76% of $H_2$ produced by the PDH reaction. To achieve this high $H_2$ removal rate, several parameters were considered and optimized, including the sweeping flow rate, WHSV as well as the membrane reactor geometry. High sweeping flow rates of 24 cm$^3$/min were used to maximize selective $H_2$ removal, as the $H_2$ diffusion driving force becomes higher. A low WHSV of 0.86 h$^{-1}$ was used to closely match the dehydrogenation reaction rate to the $H_2$ transport rate. The data show that when $O_2$ is present in the sweeping gas, $H_2$ removal is improved to 86-96%, with $H_2$ being almost completely depleted from the reaction zone. Without intending to be bound by theory, it is believed that this higher $H_2$ removal is due to an even higher driving force when $O_2$ is present, prompted by the combustion of $H_2$ and its subsequent consumption ($H_2$ removed from the tube side and is now consumed on the shell side) which leads to an increase in the $H_2$ partial pressure driving force gradient.

Figure 25C:
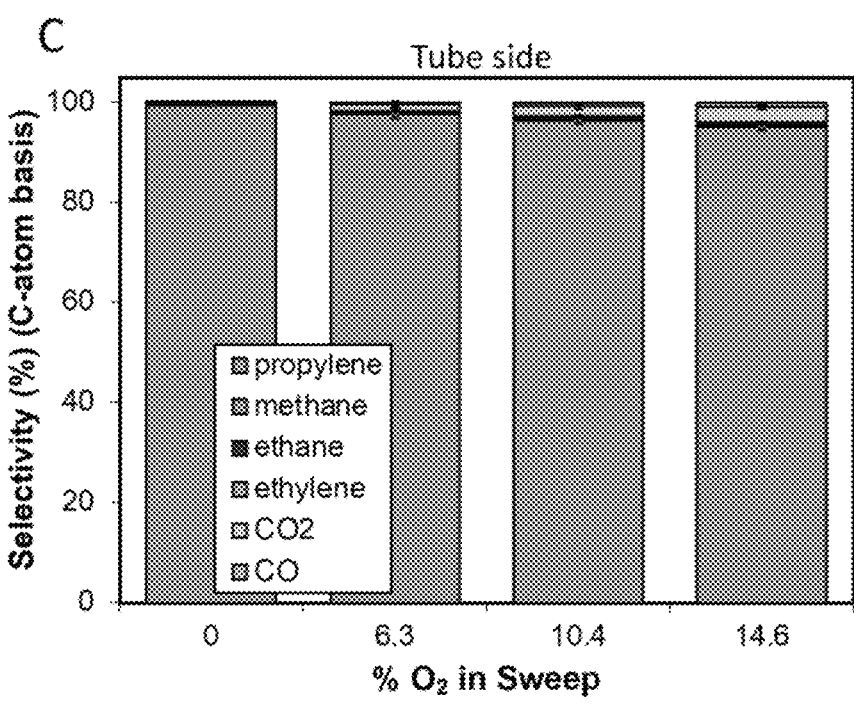
FIG. 25C is a graph showing tube-side product distribution on a C-atom basis.
Figure 25D:
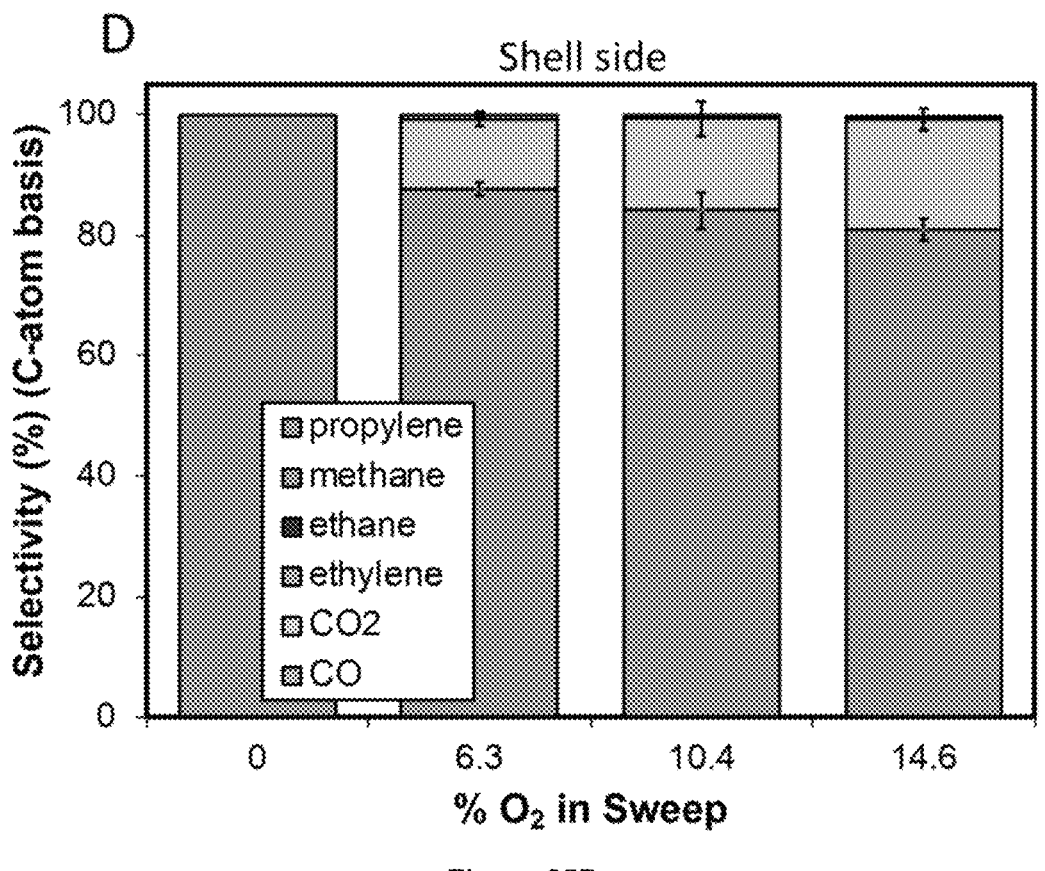
FIG. 25D is a graph showing shell side product distribution on a C-atom basis. In the graphs of FIG. 25, reaction temperature was 500° C., $P_{C3H8}$=1 atm, WHSV=0.86 hours$^-$1, and sweep:feed ratio=12.

The product distributions on a carbon-atom basis for both the tube and shell sides are shown in FIGS. 25C and 25D. Although using $O_2$ in the sweeping gas improved propane conversion, it decreased propylene selectivity on the tube side from 99% to 95% when 15% $O_2$ was used. Because the membrane operates in a Knudsen separation regime, $H_2$ removal is associated with backflow of shell side gases to the tube side. As mentioned above, $N_2$ backflow to the tube side was monitored and accounted for in equilibrium propane conversion calculations. Similarly, when $O_2$ was used in the sweeping gas, $CO_x$ products (CO and $CO_2$) were monitored on both sides of the catalyst system and accounted for in product distribution calculations. For the 0% $O_2$ case, the main reaction product was propylene (>99% selectivity) with very little propane cracking and hydrogenation side products (methane, ethane, and ethylene) on both the tube and shell sides. This high propylene selectivity, specifically in the catalyst system, is an advantage to lower temperature operation of PDH which is limited to membrane reactors, as otherwise low temperatures limit equilibrium conversion in traditional packed bed reactors. The data show that when $O_2$ is present in the sweeping gas, $CO_x$ products start to form, especially on the shell side. Since $O_2$ and $CO_2$ have similar kinetic diameters and the $SiO_2/Al_2O_3$ membrane used in this system performs selective separation close to the Knudsen separation limits (molecule size dependent), it is possible that either the $CO_x$ products or $O_2$ backflowed to the tube side, where $O_2$ reacted with propane and formed $CO_x$. At 15% $O_2$ in the inert sweeping gas, $CO_x$ products constituted 4% of the product distribution on the tube side and 19% on the shell side, with $CO_2$ being the main product. The amount of C-based products diffusing from the tube to the shell side was calculated to be 9-18% for the different amounts of $O_2$ fed in the sweeping gas.

Figure 26A:
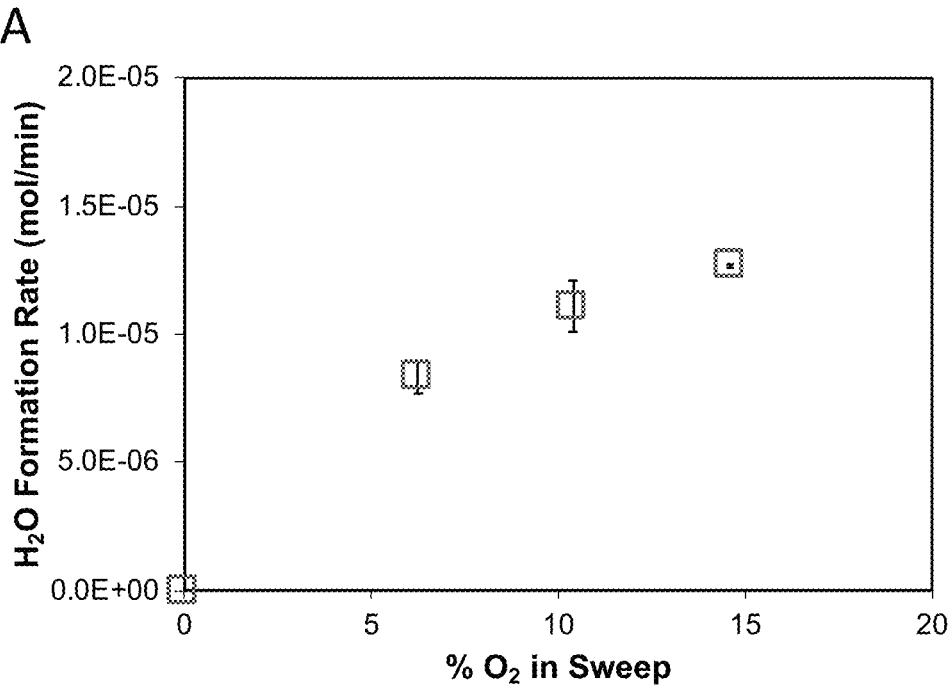
FIG. 26A is a graph showing water formation rate calculated on the shell side of a catalyst system in accordance with the disclosure as a function of % $O_2$ in the sweeping gas.
Figure 26B:
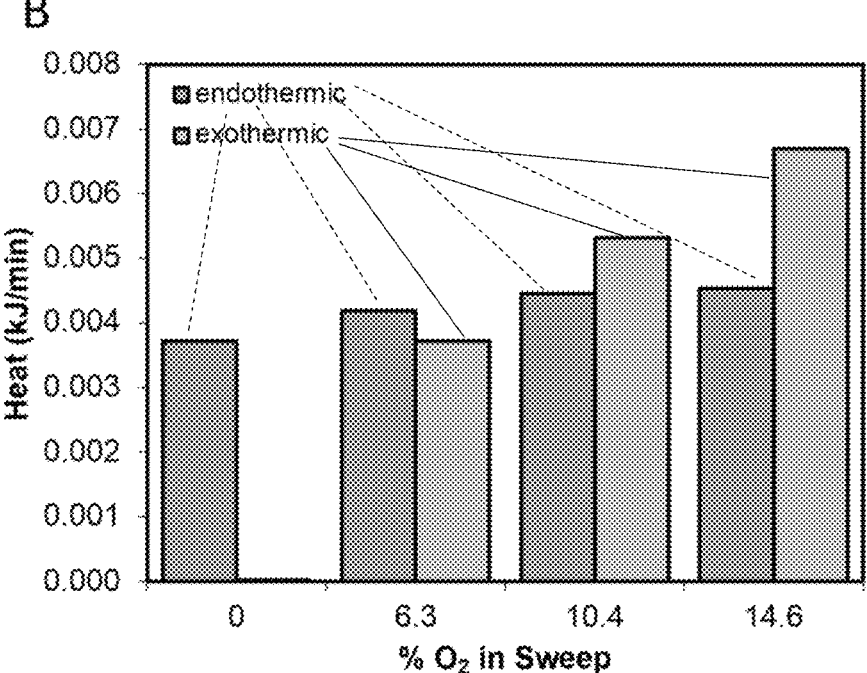
FIG. 26B is a graph showing heat requirement for propane dehydrogenation and heat release from combustion of $H_2$ and propane oxidation as a function of % $O_2$ in the sweeping gas.

The water formation rates at the different $O_2$ amounts were calculated using a humidity sensor, by monitoring the relative humidity in the outlet shell side stream. FIG. 26A shows measured water formation rates at the different $O_2$ amounts in the sweeping gas. Water formation increased as $O_2$ levels were increased, corroborating higher $H_2$ removal shown in FIG. 5B. Using these water formation rates, material balances and production rates, and heats of reactions for all endothermic and exothermic reactions present in the catalyst/membrane system, a heat analysis was performed to determine the feasibility of thermoneutral PDH operation (calculation details are included in the methods section). FIG. 26B shows the heat requirement mainly by PDH and heat release from oxidation reactions at 0-15% $O_2$ in the sweeping gas. When no $O_2$ is present in the sweep (0% $O_2$), the main reaction is endothermic PDH, and therefore, the heat flow calculated is required by the reaction and represented by the red vertical bar. When 6% $O_2$ is used in the sweeping gas, heat release by the exothermic oxidation reactions is close to matching the heat requirement by PDH (providing ~90% of the heat needed). This is supported by the increase in $H_2$ removal (FIG. 5B) and the water and $CO_x$ formation rates detected and measured. At 10-15% $O_2$ in the sweeping gas, heat release surpasses the heat requirement by PDH especially at 15% $O_2$ (supported by the highest $H_2$ removal levels and highest formation rates of water and $CO_x$ products). These heat calculation results confirm that thermoneutral operation of PDH in a catalyst system is possible by coupling PDH to exothermic oxidation reactions using mild oxidative conditions on the outer shell side of the catalyst system and allowing for heat exchange.

$H_2$ removal was calculated using the remaining amounts of propylene and $H_2$ on the tube side (Equation). The humidity level on the shell side was measured using a humidity sensor (Traceable Hygrometer) and used to calculate the water formation rates (Equation 10).

$$H_2 \text{ Removal } (\%) = (1 - \frac{P_{H_2}}{P_{propylene}}) \times 100 \qquad \text{Equation 9}$$

$$H_2O \text{ formation rate} = \frac{P_{sat}}{P} \times \frac{\text{Relative Humidity}}{100} \times F_{shell,out} \qquad \text{Equation 10}$$

Heat Calculation Methods

The heat requirement by, mainly, the endothermic PDH reaction and the heat release by the exothermic $H_2$ oxidation and oxidative PDH (as per formation of $CO_x$ products) reactions were calculated. The calculation was carried out by first using compound heats of formation and heat capacities at standard conditions (obtained from the National Institute of Standards and Technology (NIST) Chemistry WebBook) as well as their stoichiometric coefficients to calculate the enthalpies of reaction at the PDH temperature. In this calculation, the standard heat capacities were assumed to be independent of temperature. Next, using the experimentally measured product formation rates (taking stoichiometry into account) and the calculated enthalpies of reaction, the heat requirement by endothermic reactions and the heat release by exothermic reactions were calculated, summed into an endothermic or exothermic category, and compared. Note that because $SiO_2/Al_2O_3$ membrane operates in the Knudsen diffusion regime, some of the gases backflow between the tube and shell sides. Therefore, the tube and shell side outlet flow rates and compositions were determined separately using a bubble flow meter and the GC, respectively. The heats (required or released) were then calculated and compiled into endothermic or exothermic total terms (from both tube and shell sides). The products analyzed were assumed to form by one-step reactions included with the calculated enthalpies of reaction shown below.

| | |
|---|---|
| $\Delta H_f = H_f^\circ + C_p^\circ (T - T_\circ)$ | Equation 11 |
| $\Delta H_{rxn} = \Sigma v_i \Delta H_{f,i}$ | Equation 12 |
| $C_3H_8 \rightarrow C_3H_6 + H_2$ | $\Delta H_{rxn} = 134$ kJ/mol |
| $C_3H_8 \rightarrow C_2H_4 + CH_4$ | $\Delta H_{rxn} = 85$ kJ/mol |
| $C_2H_4 + H_2 \rightarrow C_2H_6$ | $\Delta H_{rxn} = -145$ KJ/mol |
| $C_3H_8 + 3.5O_2 \rightarrow 3CO + 4H_2O$ | $\Delta H_{rxn} = -506$ kJ/mol |
| $C_3H_8 + 5O_2 \rightarrow 3CO_2 + 4H_2O$ | $\Delta H_{rxn} = -1965$ kJ/mol |
| $H_2 + O_2 \rightarrow H_2O$ | $\Delta H_{rxn} = -246$ kJ/mol |

The foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In the case of conflict, the present description, including definitions, will control.

Throughout the specification, where the compounds, compositions, methods, and/or processes are described as including components, steps, or materials, it is contemplated that the compounds, compositions, methods, and/or processes can also comprise, consist essentially of, or consist of any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

Chen, S. et al. Propane dehydrogenation: catalyst development, new chemistry, and emerging technologies. *Chem Soc Rev* 50, 3315-3354 (2021).

J. H. B. Sattler, J., Ruiz-Martinez, J., Santillan-Jimenez, E. & M. Weckhuysen, B. Catalytic Dehydrogenation of Light Alkanes on Metals and Metal Oxides. *Chem Rev* 114, 10613-10653 (2014).

National Academies of Sciences and Medicine, E. The Changing Landscape of Hydrocarbon Feedstocks for Chemical Production: Implications for Catalysis: Proceedings of a Workshop. (The National Academies Press, 2016). doi:10.17226/23555.

U.S. Department of Energy. Natural Gas Flaring and Venting: State and Federal Regulatory Overview, Trends, and Impacts. (2019).

Mansoor, R. & Tahir, M. Recent Developments in Natural Gas Flaring Reduction and Reformation to Energy-Efficient Fuels: A Review. *Energy & Fuels* 35, 3675-3714 (2021).

Zhao, Z. -J., Chiu, C. & Gong, J. Molecular understandings on the activation of light hydrocarbons over heterogeneous catalysts. *Chem Sci* 6, 4403-4425 (2015).

Jiang, F. et al. Propane Dehydrogenation over Pt/TiO2— Al2O3 Catalysts. *ACS Catal* 5, 438-447 (2014).

Wang, J. et al. On the Role of Sn Segregation of Pt—Sn Catalysts for Propane Dehydrogenation. *ACS Catal* 0, 4401-4410 (2021).

Iglesias-Juez, A. et al. A combined in situ time-resolved UV—Vis, Raman and high-energy resolution X-ray absorption spectroscopy study on the deactivation behavior of Pt and PtSn propane dehydrogenation catalysts under industrial reaction conditions. *J Catal* 276, 268-279 (2010).

Bhasin, M. M., McCain, J. H., Vora, B. v, Imai, T. & Pujadó, P. R. Dehydrogenation and oxydehydrogenation of paraffins to olefins. *Appl Catal A Gen* 221, 397-419 (2001).

Armor, J. N. Applications of catalytic inorganic membrane reactors to refinery products. *J Memb Sci* 147, 217-233 (1998).

Weyten, H., Luyten, J., Keizer, K., Willems, L. & Leysen, R. Membrane performance: the key issues for dehydrogenation reactions in a catalytic membrane reactor. *Catal Today* 56, 3-11 (2000).

Ziaka, Z. D., Minet, R. G. & Tsotsis, T. T. A high temperature catalytic membrane reactor for propane dehydrogenation. *J Memb Sci* 77, 221-232 (1993).

P. Collins, J. et al. Catalytic Dehydrogenation of Propane in Hydrogen Permselective Membrane Reactors. *Industrial & Engineering Chemistry Research* 35, 4398-4405 (1996).

Gbenedio, E., Wu, Z., Hatim, I., Kingsbury, B. F. K. & Li, K. A multifunctional Pd/alumina hollow fibre membrane reactor for propane dehydrogenation. *Catal Today* 156, 93-99 (2010).

Pati, S., Dewangan, N., Wang, Z., Jangam, A. & Kawi, S. Nanoporous Zeolite-A Sheltered Pd-Hollow Fiber Catalytic Membrane Reactor for Propane Dehydrogenation. *ACS Appl Nano Mater* 3, 6675-6683 (2020).

Wang, Z. et al. High H2 permeable SAPO-34 hollow fiber membrane for high temperature propane dehydrogenation application. *AIChE Journal* 66, e16278 (2020).

Kim, S. -J. et al. Thin Hydrogen-Selective SAPO-34 Zeolite Membranes for Enhanced Conversion and Selectivity in Propane Dehydrogenation Membrane Reactors. *Chemistry of Materials* 28, 4397-4402 (2016).

Schäfer, R., Noack, M., Kölsch, P., Stöhr, M. & Caro, J. Comparison of different catalysts in the membrane-supported dehydrogenation of propane. *Catal Today* 82, 15-23 (2003).

Weyten, H., Keizer, K., Kinoo, A., Luyten, J. & Leysen, R. Dehydrogenation of propane using a packed-bed catalytic membrane reactor. *AIChE Journal* 43, 1819-1827 (1997).

Li, C. & Wang, G. Dehydrogenation of light alkanes to mono-olefins. *Chem Soc Rev* 50, 4359-4381 (2021).

22. Li, Q. et al. Coke Formation on Pt—Sn/Al2O3 Catalyst in Propane Dehydrogenation: Coke Characterization and Kinetic Study. *Top Catal* 54, 888 (2011).

Sattler, A. et al. Catalytic limitations on alkane dehydrogenation under H2 deficient conditions relevant to membrane reactors. *Energy Environ Sci* 15, 2120-2129 (2022).

Saerens, S. et al. The Positive Role of Hydrogen on the Dehydrogenation of Propane on Pt(111). *ACS Catal* 7, 7495-7508 (2017).

25. Handbook of Petroleum Refining Processes. (McGraw-Hill Education, 2016). Motagamwala, A. H., Almallahi, R., Wortman, J., Igenegbai, V. O. & Linic, S. Stable and selective catalysts for propane dehydrogenation operating at thermodynamic limit. *Science* (1979) 373, 217 (2021).

Choi, S. -W. et al. Modeling and process simulation of hollow fiber membrane reactor systems for propane dehydrogenation. *AIChE Journal* 63, 4519-4531 (2017).

Kärger, J., Ruthven, D. M. & Theodorou, D. N. Diffusion in Nanoporous Materials. in *Diffusion in Nanoporous Materials* vol. 1 85-110 (Wiley-VCH, 2012).

Battersby, S. et al. An analysis of the Peclet and Damkohler numbers for dehydrogenation reactions using molecular sieve silica (MSS) membrane reactors. *Catal Today* 116, 12-17 (2006).

Gokhale, Y. v, Noble, R. D. & Falconer, J. L. Effects of reactant loss and membrane selectivity on a dehydrogenation reaction in a membrane-enclosed catalytic reactor. *J Memb Sci* 103, 235-242 (1995).

Moon, W. S. & Park, S. bin. Design guide of a membrane for a membrane reactor in terms of permeability and selectivity. *J Memb Sci* 170, 43-51 (2000).

Choi, S. -W. et al. Material properties and operating configurations of membrane reactors for propane dehydrogenation. *AIChE Journal* 61, 922-935 (2015).

Larsson, M., Hultén, M., Blekkan, E. A. & Andersson, B. The Effect of Reaction Conditions and Time on Stream on the Coke Formed during Propane Dehydrogenation. *J Catal* 164, 44-53 (1996).

Lobera, M. P., Téllez, C., Herguido, J. & Menéndez, M. Transient kinetic modelling of propane dehydrogenation over a Pt—Sn—K/Al2O3 catalyst. *Appl Catal A Gen* 349, 156-164 (2008).

Rebo, H. P., Blekkan, E. A., Bednářová, L. & Holmen, A. Deactivation of Pt—Sn catalyst in propane dehydrogenation. in *Studies in Surface Science and Catalysis* (eds. Delmon, B. & Froment, G. F.) vol. 126 333-340 (Elsevier, 1999).

van Sint Annaland, M., Kuipers, J. A. M. & van Swaaij, W. P. M. A kinetic rate expression for the time-dependent coke formation rate during propane dehydrogenation over a platinum alumina monolithic catalyst. *Catal Today* 66, 427-436 (2001).

Wang, P. et al. Stabilizing the isolated Pt sites on PtGa/Al2O3 catalyst via silica coating layers for propane dehydrogenation at low temperature. *Appl Catal B* 300, 120731 (2022).

Song, Z. et al. Improved Effect of Fe on the Stable NiFe/Al2O3 Catalyst in Low-Temperature Dry Reforming of Methane. *Industrial & Engineering Chemistry Research* 59, 17250-17258 (2020).

T, H. R. et al. First-principles design of a single-atom-alloy propane dehydrogenation catalyst. *Science* (1979) 372, 1444-1447 (2021).

Qu, Y. et al. Low-Temperature Direct Dehydrogenation of Propane over Binary Oxide Catalysts: Insights into Geometric Effects and Active Sites. *ACS Sustainable Chemistry & Engineering* 9, 12755-12765 (2021).

A. H. Motagamwala, R. Almallahi, J. Wortman, V. O. Igenegbai, S. Linic, Stable and selective catalysts for propane dehydrogenation operating at thermodynamic limit. *Science* (1979). 373, 217 (2021).

H. Weyten, K. Keizer, A. Kinoo, J. Luyten, R. Leysen, Dehydrogenation of propane using a packed-bed catalytic membrane reactor. *AIChE Journal.* 43, 1819-1827 (1997).

S. -J. Kim, Y. Liu, J. S. Moore, R. S. Dixit, J. G. Pendergast, D. Sholl, C. W. Jones, S. Nair, Thin Hydrogen-Selective SAPO-34 Zeolite Membranes for Enhanced Conversion and Selectivity in Propane Dehydrogenation Membrane Reactors. *Chemistry of Materials.* 28, 4397-4402 (2016).

S. Pati, N. Dewangan, Z. Wang, A. Jangam, S. Kawi, Nanoporous Zeolite-A Sheltered Pd-Hollow Fiber Catalytic Membrane Reactor for Propane Dehydrogenation. *ACS Appl Nano Mater.* 3, 6675-6683 (2020).

J. P. Collins, R. W. Schwartz, R. Sehgal, T. L. Ward, C. J. Brinker, G. P. Hagen, C. A. Udovich, Catalytic Dehydrogenation of Propane in Hydrogen Permselective Membrane Reactors. *Industrial & Engineering Chemistry Research.* 35,4398-4405 (1996).

E. Gbenedio, Z. Wu, I. Hatim, B. F. K. Kingsbury, K. Li, A multifunctional Pd/alumina hollow fibre membrane reactor for propane dehydrogenation. *Catal Today.* 156,93-99 (2010).

Z. Wu, I. M. D. Hatim, B. F. K. Kingsbury, E. Gbenedio, K. Li, A novel inorganic hollow fiber membrane reactor for catalytic dehydrogenation of propane. *AIChE Journal.* 55, 2389-2398 (2009).

O. A. Bariås, A. Holmen, E. A. Blekkan, Propane Dehydrogenation over Supported Pt and Pt—Sn Catalysts: Catalyst Preparation, Characterization, and Activity Measurements. *J Catal.* 158, 1-12 (1996).

J. Salmones, J. -A. Wang, J. A. Galicia, G. Aguilar-Rios, H2 reduction behaviors and catalytic performance of bimetallic tin-modified platinum catalysts for propane dehydrogenation. *J Mol Catal A Chem.* 184, 203-213 (2002).

Y. Zhou, S. M. Davis, Low-Pressure Dehydrogenation of Light Paraffins (1993). N. Kaylor, R. J. Davis, Propane dehydrogenation over supported Pt—Sn nanoparticles. *J Catal.* 367, 181-193 (2018).

Y. Zhang, Y. Zhou, L. Huang, M. Xue, S. Zhang, Sn-Modified ZSM-5 As Support for Platinum Catalyst in Propane Dehydrogenation. *Industrial & Engineering Chemistry Research.* 50, 7896-7902 (2011).

13. P. L. de Cola, R. Gläser, J. Weitkamp, Non-oxidative propane dehydrogenation over Pt—Zn-containing zeolites. *Appl Catal A Gen.* 306, 85-97 (2006).

Otroshchenko, T., Jiang, G., Kondratenko, V. A., Rodemerck, U. & Kondratenko, E. v. Current status and perspectives in oxidative, non-oxidative and CO2-mediated dehydrogenation of propane and isobutane over metal oxide catalysts. *Chem Soc Rev* 50, 473-527 (2021).

Agarwal, A., Sengupta, D. & El-Halwagi, M. Sustainable Process Design Approach for On-Purpose Propylene Production and Intensification. *ACS Sustainable Chemistry & Engineering* 6, 2407-2421 (2018).

Chen, S. et al. Propane dehydrogenation: catalyst development, new chemistry, and emerging technologies. *Chem Soc Rev* 50, 3315-3354 (2021).

Zhao, Z. -J., Chiu, C. & Gong, J. Molecular understandings on the activation of light hydrocarbons over heterogeneous catalysts. *Chem Sci* 6, 4403-4425 (2015). Jiang, F. et al. Propane Dehydrogenation over Pt/TiO2—Al2O3 Catalysts. *ACS Catal* 5, 438-447 (2014).

Wang, J. et al. On the Role of Sn Segregation of Pt—Sn Catalysts for Propane Dehydrogenation. *ACS Catal* 0, 4401-4410 (2021).

Iglesias-Juez, A. et al. A combined in situ time-resolved UV-Vis, Raman and high-energy resolution X-ray absorption spectroscopy study on the deactivation behavior of Pt and PtSn propane dehydrogenation catalysts under industrial reaction conditions. *J Catal* 276, 268-279 (2010).

J. H. B. Sattler, J., Ruiz-Martinez, J., Santillan-Jimenez, E. & M. Weckhuysen, B. Catalytic Dehydrogenation of Light Alkanes on Metals and Metal Oxides. *Chem Rev* 114, 10613-10653 (2014).

Grant, J. T. et al. Selective oxidative dehydrogenation of propane to propene using boron nitride catalysts. *Science* 354, 1570-1573 (2016).

A. Carrero, C., Schloegl, R., E. Wachs, I. & Schomaecker, R. Critical Literature Review of the Kinetics for the Oxidative Dehydrogenation of Propane over Well-Defined Supported Vanadium Oxide Catalysts. *ACS Catal* 4, 3357-3380 (2014).

Liu, L. et al. Structural modulation and direct measurement of subnanometric bimetallic PtSn clusters confined in zeolites. *Nat Catal* 3, 628-638 (2020).

Sun, Q. et al. Subnanometer Bimetallic Platinum-Zinc Clusters in Zeolites for Propane Dehydrogenation. *Angewandte Chemie International Edition* 59, 19450-19459 (2020).

Motagamwala, A. H., Almallahi, R., Wortman, J., Igenegbai, V. O. & Linic, S. Stable and selective catalysts for propane dehydrogenation operating at thermodynamic limit. *Science* (1979) 373,217 (2021).

Ziaka, Z. D., Minet, R. G. & Tsotsis, T. T. A high temperature catalytic membrane reactor for propane dehydrogenation. *J Memb Sci* 77, 221-232 (1993).

P. Collins, J. et al. Catalytic Dehydrogenation of Propane in Hydrogen Permselective Membrane Reactors. *Industrial & Engineering Chemistry Research* 35,4398-4405 (1996).

Gbenedio, E., Wu, Z., Hatim, I., Kingsbury, B. F. K. & Li, K. A multifunctional Pd/alumina hollow fibre membrane reactor for propane dehydrogenation. *Catal Today* 156, 93-99 (2010).

Schäfer, R., Noack, M., Kölsch, P., Stöhr, M. & Caro, J. Comparison of different catalysts in the membrane-supported dehydrogenation of propane. *Catal Today* 82, 15-23 (2003).

Weyten, H., Luyten, J., Keizer, K., Willems, L. & Leysen, R. Membrane performance: the key issues for dehydrogenation reactions in a catalytic membrane reactor. *Catal Today* 56,3-11 (2000).

Saerens, S. et al. The Positive Role of Hydrogen on the Dehydrogenation of Propane on Pt(111). *ACS Catal* 7, 7495-7508 (2017).

Sattler, A. et al. Catalytic limitations on alkane dehydrogenation under H2 deficient conditions relevant to membrane reactors. *Energy Environ Sci* 15,2120-2129 (2022).

Morejudo, S. H. et al. Direct conversion of methane to aromatics in a catalytic co-ionic membrane reactor. *Science* 353, 563-566 (2016).

Sakbodin, M. et al. Direct Nonoxidative Methane Conversion in an Autothermal Hydrogen-Permeable Membrane Reactor. *Adv Energy Mater* 2102782 (2021).

Feng, Y., Luo, J. -L. & Chuang, K. T. Carbon deposition during propane dehydrogenation in a fuel cell. *J Power Sources* 167, 486-490 (2007).

Kim, S. -J. et al. Thin Hydrogen-Selective SAPO-34 Zeolite Membranes for Enhanced Conversion and Selectivity in Propane Dehydrogenation Membrane Reactors. *Chemistry of Materials* 28, 4397-4402 (2016).

Choi, S. -W. et al. Modeling and process simulation of hollow fiber membrane reactor systems for propane dehydrogenation. *AIChE Journal* 63, 4519-4531 (2017). de Vos, R. M. & Verweij, H. High-Selectivity, High-Flux Silica Membranes for Gas Separation. *Science* (1979) 279,1710 (1998).

Pati, S., Dewangan, N., Wang, Z., Jangam, A. & Kawi, S. Nanoporous Zeolite-A Sheltered Pd-Hollow Fiber Catalytic Membrane Reactor for Propane Dehydrogenation. *ACS Appl Nano Mater* 3, 6675-6683 (2020).

Weyten, H., Keizer, K., Kinoo, A., Luyten, J. & Leysen, R. Dehydrogenation of propane using a packed-bed catalytic membrane reactor. *AIChE Journal* 43, 1819-1827 (1997).

N. Pham, H., J. H. B. Sattler, J., M. Weckhuysen, B. & K. Datye, A. Role of Sn in the Regeneration of Pt/γ-Al2O3 Light Alkane Dehydrogenation Catalysts. *ACS Catal* 6, 2257-2264 (2016).

Deng, L., Zhou, Z. & Shishido, T. Behavior of active species on Pt—Sn/SiO2 catalyst during the dehydrogenation of propane and regeneration. *Appl Catal A Gen* 117826 (2020).

Sun, C. et al. A comparative study on different regeneration processes of Pt—Sn/γ-Al2O3 catalysts for propane dehydrogenation. *Journal of Energy Chemistry* 27, 311-318 (2018).

Larsson, M., Hultén, M., Blekkan, E. A. & Andersson, B. The Effect of Reaction Conditions and Time on Stream on the Coke Formed during Propane Dehydrogenation. *J Catal* 164, 44-53 (1996).

Lobera, M. P., Téllez, C., Herguido, J. & Menéndez, M. Transient kinetic modelling of propane dehydrogenation over a Pt—Sn—K/Al2O3 catalyst. *Appl Catal A Gen* 349,156-164 (2008).

Rebo, H. P., Blekkan, E. A., Bednářová, L. & Holmen, A. Deactivation of Pt—Sn catalyst in propane dehydrogenation. in *Studies in Surface Science and Catalysis* (eds. Delmon, B. & Froment, G. F.) vol. 126 333-340 (Elsevier, 1999).

Gu, Y., Hacarlioglu, P. & Oyama, S. T. Hydrothermally stable silica—alumina composite membranes for hydrogen separation. *J Memb Sci* 310, 28-37 (2008).

Saito, T., Seshimo, M., Akamatsu, K., Miyajima, K. & Nakao, S. Effect of physically adsorbed water molecules on the H2-selective performance of a silica membrane prepared with dimethoxydiphenylsilane and its regeneration. *J Memb Sci* 392-393, 95-100 (2012).

Gu, Y. & Oyama, S. T. Permeation properties and hydrothermal stability of silica—titania membranes supported on porous alumina substrates. *J Memb Sci* 345, 267-275 (2009).

What is claimed is:

1. A catalyst system for a dehydrogenation reaction, comprising:

a hollow fiber membrane comprising an outer support tube formed of a porous support material and a separation layer formed on an inner surface of the support tube such that the separation layer covers the inner surface of the support tube, the separation layer comprising $SiO_2$; and a dehydrogenation catalyst packed inside the hollow fiber membrane, the dehydrogenation catalyst comprising $Pt_1Sn_1$ arranged on a $SiO_2$ support, wherein a ratio of a surface area to the volume of the catalyst system is about 500 $m^2/m^3$ to about 3000 $m^2/m^3$ and an amount of catalysts exposed on the membrane surface of about 300 $g/m^2$ to about 1500 $g/m^2$.

2. The catalyst system of claim 1, wherein the support tube comprises at least two layers, an outer layer defining an outer surface of the support tube and an inner layer disposed between the outer layer and the separation layer, wherein the outer layer has an average pore size that is larger than an average pore size of the inner layer.

3. The catalyst system of claim 2, wherein the outer layer has a thickness of about 250 micrometers to about 750 micrometers and/or the outer layer has an average pore size of about 100 nm to about 500 nm.

4. The catalyst system of claim 2, wherein the inner layer has a thickness of about 0.5 micrometers to about 20 micrometers and/or the inner layer has an average pore size of about 5 nm to about 50 nm.

5. The catalyst system of claim 1, wherein the support tube is formed of $Al_2O_3$.

6. The catalyst system of claim 1, wherein the support tube has an outer diameter of about 1.5 mm to about 6 mm and/or the support tube has a wall thickness of about 0.5 mm to about 1.5 mm.

7. The catalyst system of claim 1, wherein the separation layer has a thickness of about 20 nm to about 500 nm and/or the separation layer has an average pore size of about 2 nm to about 20 nm.

8. The catalyst system of claim 1, wherein the separation layer is a composite silica material comprising $SiO_2$ and one or more of alumina, titania, zirconia, and zeolite materials.

9. The catalyst system of any claim 1, wherein the catalyst comprises $Pt_1Sn_1$ nanoparticles arranged on a $SiO_2$ support.

10. A dehydrogenation process catalyzed by the catalyst system of claim 1, comprising flowing a reactant source through the catalyst system such that the propane source flows in contact with the catalyst packed within the hollow fiber membrane and upon contact with the catalyst is selectively dehydrogenated, and $H_2$ generated during the selective dehydrogenation is selectively removed through the separation layer, wherein the process has a selectivity of at least 90%.

11. The dehydrogenation process of claim 10, comprising heating the catalyst system to a temperature of about 400° C. to about 600° C. while flowing the propane source through the catalyst system.

12. The dehydrogenation process of claim 10, wherein the process is performed with no added $H_2$.

13. The dehydrogenation process of claim 10, further comprising flowing an inert sweeping gas over an outer surface of the tube to carry away $H_2$ separated from the dehydrogenation reaction, optionally wherein the inert gas is Ar, He, Ne, Kr, Xe, or Rn.

14. The dehydrogenation process of claim 10, wherein the reactant source comprises propane and upon contact with the catalyst, the propane is selectively dehydrogenated to propylene.

15. A dehydrogenation process catalyzed by the catalyst system of claim 1, comprising:

flowing a reactant source through the catalyst system such that the propane source flows in contact with the catalyst packed within the hollow fiber membrane and upon contact with the catalyst is selectively dehydrogenated, and $H_2$ generated during the selective dehydrogenation is selectively removed through the separation layer; and flowing a sweeping gas comprising $O_2$ over an outer surface of the support tube to oxidize $H_2$ separated from the dehydrogenation reaction thereby forming water and heat, wherein the process has a selectivity of at least 90%.

16. The dehydrogenation process of claim 15, wherein the oxidization of $H_2$ supplies heat to the catalyst system for heating the catalyst system to a temperature of about 400° C. to about 600° C. while flowing the propane source through the catalyst system.

17. The dehydrogenation process of claim 15, wherein the sweeping gas comprises about 6% to about 15% by volume $O_2$.

18. The dehydrogenation process of claim 15, wherein the sweeping gas further comprises an inert gas, wherein the inert gas is optionally Ar, He, Ne, Kr, Xe, or Rn.

19. The dehydrogenation process of claim 15, wherein the reactant source comprises propane and upon contact with the catalyst, the propane is selectively dehydrogenated to propylene.

20. The dehydrogenation process of claim 15, wherein the process is performed with no added $H_2$ and/or wherein the process is performed without applied heat from an external source.

* * * * *